(12) United States Patent
Froehner et al.

(10) Patent No.: US 9,974,767 B2
(45) Date of Patent: May 22, 2018

(54) STATINS IN THE TREATMENT OF MUSCULAR DYSTROPHIES AND MYOPATHIES

(71) Applicant: University of Washington, Seattle, WA (US)

(72) Inventors: Stanley C. Froehner, Seattle, WA (US); Nicholas P. Whitehead, Seattle, WA (US)

(73) Assignee: University of Washington, Seattle, WA (US)

( * ) Notice: Subject to any disclaimer, the term of this patent is extended or adjusted under 35 U.S.C. 154(b) by 0 days. days.

(21) Appl. No.: 14/798,877

(22) Filed: Jul. 14, 2015

(65) Prior Publication Data
US 2016/0008320 A1   Jan. 14, 2016

Related U.S. Application Data

(60) Provisional application No. 62/024,135, filed on Jul. 14, 2014.

(51) Int. Cl.

| | |
|---|---|
| A61K 31/35 | (2006.01) |
| A61K 31/21 | (2006.01) |
| A61K 31/40 | (2006.01) |
| A61K 31/366 | (2006.01) |
| A61K 45/06 | (2006.01) |
| A61K 31/519 | (2006.01) |
| A61K 31/4985 | (2006.01) |
| A61K 31/405 | (2006.01) |
| A61K 31/4418 | (2006.01) |
| A61K 9/00 | (2006.01) |

(52) U.S. Cl.
CPC .......... *A61K 31/366* (2013.01); *A61K 9/0053* (2013.01); *A61K 31/40* (2013.01); *A61K 31/405* (2013.01); *A61K 31/4418* (2013.01); *A61K 31/4985* (2013.01); *A61K 31/519* (2013.01); *A61K 45/06* (2013.01)

(58) Field of Classification Search
CPC .... A61K 31/366; A61K 31/40; A61K 31/405; A61K 31/4418; A61K 31/4985; A61K 31/519; A61K 45/06; A61K 9/0053
USPC ... 514/250, 252.16, 460, 423, 451, 510, 907
See application file for complete search history.

(56) References Cited

U.S. PATENT DOCUMENTS

| | | | |
|---|---|---|---|
| 7,217,720 B2 * | 5/2007 | Meissner | A61K 31/473 514/252.16 |
| 8,575,222 B2 | 11/2013 | Clementi et al. | |
| 2004/0013643 A1 * | 1/2004 | Mach | A61K 31/225 424/85.6 |
| 2011/0027371 A1 | 2/2011 | Cooepr et al. | |
| 2012/0270933 A1 | 10/2012 | Phelps et al. | |
| 2013/0059801 A1 * | 3/2013 | Milne | C07H 13/04 514/23 |
| 2014/0256644 A1 | 9/2014 | Ward et al. | |
| 2015/0065553 A1 | 3/2015 | Pavliv et al. | |
| 2015/0080328 A1 * | 3/2015 | Villarreal | A61K 31/353 514/34 |
| 2015/0164833 A1 | 6/2015 | Kuang et al. | |

FOREIGN PATENT DOCUMENTS

WO   WO 2008133884 A2 *  11/2008   ......... A61K 31/4439

OTHER PUBLICATIONS

Shitara et al., "Pharmacokinetic and pharmacodynamic alterations of 3-hydroxy-3-methylglutaryl coenzyme A (HMG-CoA) reductase inhibitors: Drug—drug interactions and interindividual differences in transporter and metabolic enzyme functions", 2006, Pharmacology & Therapeutics, 112 (1), pp. 71-105.*
Sivakumar Sathasivam, "Statin induced myotoxicity", European Journal of Internal Medicine, 2012, 23(4), pp. 317-324.*
Keen et al., "Statin myopathy: the fly in the ointment for the prevention of cardiovascular disease in the 21st century?", Expert Opinion on Drug Safety, 2014, 13(9), pp. 1227-1239.*
Rosenson et al., "An assessment by the Statin Muscle Safety Task Force: 2014 update", Journal of Clinical Lipidology, May-Jun. 2014, 8 (3, Supplement), pp. S58-S71.*
Antoniades et al., "Preoperative Atorvastatin Treatment in CABG Patients Rapidly Improves Vein Graft Redox State by Inhibition of Rac1 and NADPH-Oxidase Activity", Circulation, 122: S66-S73 (2010).
Asai et al., "Primary Role of Functional Ischemia, Quantitative Evidence for the Two-Hit Mechanism, and Phosphodiesterase-55 Inhibitor Therapy in Mouse Muscular Dystrophy", PLoS One, 2(8): e806 (2007).
Beck et al., "Diastolic function parameters are improved by the addition of simvastatin to enalapril-based treatment in hypertensive individuals", Atherosclerosis, 222: 444-448 (2012).
Blanco-Rivero et al., "Rosuvastatin restored adrenergic and nitrergic function in mesenteric arteries from obese rats", British Journal of Pharmacology, 162: 271-285 (2011).
Cowled et al., "Statins Inhibit Neutriphil Infiltration in Skeletal Muscle Reperfusion Injury", Journal of Surgical Research, 141: 267-276 (2007).
Dalaklioglu et al., "Pravastatin improves the impaired nitric oxide-mediated neurogenic and endothelium-dependent relaxation of corpus cavernosum in aged rats", The Aging Male, 17(4): 259-266 (2014).
El-Azab et al., "Role of simvastatin and/or antioxidant vitamins in therapeutic angiogenesis in experimental diabetic hindlimb ischemia: effects on capillary density, angiogenesis markers, and oxidative stress", European Journal of Pharmacology, 690: 31-41 (2012).

(Continued)

*Primary Examiner* — My-Chau T. Tran
(74) *Attorney, Agent, or Firm* — Nixon Peabody LLP; Mark J. FitzGerald; Srividya Subramanian

(57) ABSTRACT

The invention provides methods and compositions for treating neuromuscular diseases including, but not limited to muscular dystrophies. It is demonstrated herein that statin drugs are therapeutic for neuromuscular disease, including, but not limited to muscular dystrophies.

16 Claims, 14 Drawing Sheets
(6 of 14 Drawing Sheet(s) Filed in Color)

(56) References Cited

OTHER PUBLICATIONS

Fukuta et al., "Statin Therapy May Be Associated With Lower Mortality in Patients With Diastolic Heart Failure", Circulation, 112: 357-363 (2005).
Gao et al., "Simvastatin Inhibits Central Sympathetic Outflow in Heart Failure by a Nitric-Oxide Synthase Mechanism", The Journal of Pharmacology and Experimental Therapeutics, 326(1): 278-285 (2008).
Ito et al., "Atorvastatin upregulates nitric oxide synthases with Rho-kinase inhibition and AKT activation in the kidney of spontaneously hypertensive rats", Journal of Hypertension, 28(11): 2278-2288 (2010).
Joy et al., "Narrative Review: Statin-Related Myopathy", Ann Intern Med, 150: 858-868 (2009).
Khairallah et al., "Microtubules Underlie Dysfunction in Duchenne Muscular Dystrophy", Physiology, 5(236): 1-10 (2012).
Koboyashi et al., "Sarcolemma-localized nNOS is required to maintain activity after mild exercise", Nature, 456: 511-515 and Supplementary Information (2008).
Kureishi et al., "The HMG-CoA reductase inhibitor simvastatin activates the protein kinase Akt and promotes angiogenesis in normocholesterolemic animals", Nature America, 6(8-9): 1004-1010 (2000).
Mu et al., "RhoA mediates defective stem cell function and heterotopic ossification in dystrophic muscle of mice", The FASEB Journal, 27: 3619-3631 (2013).
O'Gorman et al., "Systematic Review and Metaanalysis of Statins for Heterozygous Familial Hypercholesterolemia in Children: Evaluation of Cholesterol Changes and Side Effects", Pediatr Cardiol, 30: 482-489 (2009).
Ongini et al., "Nitric oxide (NO)-releasing statin derivatives, a class of drugs showing enhanced antiproliferative and anti-inflammatory properties", PNAS, 101(22): 8497-8502 (2004).
Palladino et al., "Angiogenic Impairment of the Vascular Endothelium", Arterioscler Thromb Vasc Biol, 33: 2867-2876 and Supplemental Materials (2013).
Parsons et al., "Genetic Disruption of Calcineurin Improves Skeletal Muscle Pathology and Cardiac Disease in a Mouse Model of Limb-Girdle Muscular Dystrophy". J Biol Chem, 282(13): 10068-10078 (2007).
Pedersen, "Randomised trial of cholesterol lowering in 4444 patients with coronary heart disease: the Scandinavian Simvastatin Survival Study (4S)", 344: 1383-1389 (1994).
Pedersen et al., "Follow-Up Study of Patients Randomized in the Scandinavian Simvastatin Survival Study (4S) of Cholesterol Lowering", Am J Cardiol, 86: 257-262 (2000).
Prosser et al., "X-ROS Signaling: Rapid Mechano-Chemo Transduction in Heart", Science, 333: 1440-1445 (2011).
Reagan-Shaw et al., "Dose translation from animal to human studies revisited", The FASEB Journal, 22: 659-661 (2007).
Sander et al., "Functional muscle ischemia in neuronal nitric oxide synthase-deficient skeletal muscle of children with Duchenne muscular dystrophy", PNAS, 97(25): 13818-13823 (2000).
Wehling-Henricks et al., "Neuronal Nitric Oxide Synthase-Rescue of Dystrophin/Utrophin Double Knockout Mice does not Require nNOS Localization to the Cell Membrane", PLoS One, 6(10): e25071 (2011).
Adamo et al., Sildenafil reverses cardiac dysfunction in the mdx mouse model of Duchenne muscular dystrophy, Proc Natl Acad Sci U S A 107:19079-19083 (2010).
Aiello et al., "Statin therapy is associated with superior clinical outcomes after endovascular treatment of critical limb ischemia", J Vasc Surg 55(2):371-379; discussion 380 (2012).
Cardamone et al., "Inherited myopathies and muscular dystrophies", Semin Neurol 28:250-259 (2008).
Ganga et al., "A systematic review of statin-induced muscle problems in clinical trials", American Heart Journal 168 (1):6-15 (2014).
Gazzerro et al., "Pharmacological actions of statins: a critical appraisal in the management of cancer", Pharmacol Rev. 64(1):102-146 (2012).
Hanai et al., "The muscle-specific ubiquitin liagse atrogin-1/MAFbx mediates statin-induced muscle toxicity", The Journal of Investigation 117(12):3940-3951 (2007).
Istvan et al., "Structual mechanism for statin inhibition of HMG-CoA reductase", Science 292:1160-1164 (2001).
Kirchmann et al., "Echocardiographic and electrocardiographic findings of cardiomyopathy in Duchenne and Becker-Kiener Muscular Dystrophies".
Koksoy et al., Simvastatin pretreatment reduces the severity of limb ischemia in an experimental diabetes model, J Vasc Surg 45(3):590-596 (2007).
Patel et al., Simvastatin induces regression of cardiac hypertrophy and fibrosis and improves cardiac function in a transgenic rabbit model of human hypertrophic cardiomyopathy, Circulation 104(3)317-324 (2001).
Percival et al., "Sildenafil reduces respiratory muscle weakness and fibrosis in the mdx mouse model of Duchenne muscular dystrophy", J Pathol 228(1):77-87 (2012).
Sidaway et al., Statin-induced myopathy in the rat: relationship between systemic exposure, muscle exposure and myopathy. Xenobiotica 39(1):90-98 (2009).
Wang et al., "Pleiotropic effects of statin therapy: molecular mechanisms and clinical results", Trends Mol Med 14, (1):37-44 (2008).
Whitehead et al., "Muscle damage in mdx (dystrophic) mice: role of calcium and reactive oxygen species", Proceedings of the Australian Physiological Society 36:111-117 (2005).
Whitehead et al., "N-Acetylcysteine ameliorates skeletal muscle pathophysiology in mdx mice", J Physiol 586: 2003-2014 (2008).
Whitehead et al., "Skeletal muscle NADPH oxidase is increased and triggers stretch-induced damage in the mdx mouse", PLoS One 5(2):e15354 (2010).

\* cited by examiner

STATINS IN THE TREATMENT OF MUSCULAR DYSTROPHIES AND MYOPATHIES

CROSS REFERENCE TO RELATED APPLICATIONS

This application claims benefit under 35 U.S.C. § 119(e) of U.S. Provisional No. 62/024,135, filed Jul. 14, 2014, the contents of which are incorporated herein by reference in their entirety.

STATEMENT REGARDING FEDERALLY SPONSORED RESEARCH

This invention was made with U.S. government support under 1 R21 NS 088691-01, awarded by the National Institutes of Health. The U.S. Government has certain rights in the invention.

FIELD OF THE INVENTION

The present disclosure is directed to methods of treating neuromuscular diseases with statins.

BACKGROUND

Duchenne muscular dystrophy (DMD) is a common, X-linked neuromuscular disease affecting 1 in 5000 males worldwide. DMD causes severe muscle wasting and death from respiratory and/or cardiac failure usually before 30 years of age. It is caused by mutations in the dystrophin gene, which encodes a large (427 kD) protein linking the cytoskeleton to the muscle cell membrane (sarcolemma) DMD is characterized by progressive muscle degeneration, inflammation and replacement of healthy muscle with fibrosis and fat cells. This leads to profound muscle weakness of all muscles including respiratory muscles, such as the diaphragm, and the heart. Current treatments for DMD, such as steroids, have little effect in slowing the progression of the disease and have significant side effects.

SUMMARY OF THE INVENTION

Provided herein are methods of treating or ameliorating neuromuscular disorders, such as muscular dystrophies and myopathies, comprising administering a therapeutically effective amount of a statin drug to a subject in need thereof. While statins have been tested for their ability to treat ischemic muscle diseases in animals and humans, use of these drugs for primary skeletal and cardiac myopathies has not been explored. In fact, the use of statins in disorders such as Duchenne muscular dystrophy is generally contraindicated, due to concerns about statin-induced myopathies. Therefore, the methods described herein represent a paradigm shift that uses a purportedly myopathic family of drugs to treat degenerative neuromuscular diseases, such as DMD.

Accordingly, provided herein in some aspects are methods of treating a neuromuscular disease comprising administering to a subject having or at risk for a neuromuscular disease, a therapeutically effective amount of a statin drug.

In some embodiments of these methods and all such methods described herein, the statin drug is a lipophilic statin drug.

In some embodiments of these methods and all such methods described herein, the lipophilic statin drug is selected from simvastatin, atorvastatin, cerivastatin, fluvastatin, lovastatin, and pitavastatin.

In some embodiments of these methods and all such methods described herein, the lipophilic statin drug is simvastatin.

In some embodiments of these methods and all such methods described herein, the statin drug is administered at a dose of 0.1 mg to 100 mg.

In some embodiments of these methods and all such methods described herein, the statin drug is administered as a liquid formulation.

In some embodiments of these methods and all such methods described herein, the statin drug is administered as a dissolvable or chewable tablet or as a rapidly dissolving film comprising said statin drug.

In some embodiments of these methods and all such methods described herein, the statin drug is administered in an open acid dose form.

In some embodiments of these methods and all such methods described herein, the statin drug is administered in a lactone pro-drug form.

In some embodiments of these methods and all such methods described herein, the neuromuscular disease is selected from Duchenne muscular dystrophy, Becker muscular dystrophy, Limb-girdle muscular dystrophies, Ullrich congenital muscular dystrophy, inflammatory myositis, muscle atrophy, and Amyotrophic lateral sclerosis.

In some embodiments of these methods and all such methods described herein, the subject having or at risk for a neuromuscular disease does not have/has not been previously diagnosed with high cholesterol levels or does not have/has not been previously diagnosed with a cardiovascular disease.

In some embodiments of these methods and all such methods described herein, the subject having or at risk for a neuromuscular disease does not have/has not been previously diagnosed with familial hypercholesterolaemia.

In some embodiments of these methods and all such methods described herein, the statin administration for treatment of neuromuscular disease is commenced before the subject is 10 years of age.

Also provided herein in some aspects are methods of using a rapidly dissolving tablet or film formulation of a statin drug, the methods comprising administering a rapidly dissolving tablet or film formulation to an individual with a neuromuscular disorder that impairs normal swallowing.

In some embodiments of these methods and all such methods described herein, the administering treats said neuromuscular disorder.

In some embodiments of these methods and all such methods described herein, the neuromuscular disorder is a muscular dystrophy.

In some embodiments of these methods and all such methods described herein, the statin drug is administered in combination with another agent therapeutic for said neuromuscular disease.

In some embodiments of these methods and all such methods described herein, the agent administered in combination is selected from the group consisting of a gene correction agent, an antioxidant, sildenafil, tadalafil, an agent that inhibits the formation of fibrosis, and an agent that stimulates autophagy.

In some embodiments of these methods and all such methods described herein, the antioxidant is N-acetylcysteine, N-acetylcysteine ethyl ester, or bucillamine.

Definitions

Unless otherwise defined herein, scientific and technical terms used in connection with the present application shall have the meanings that are commonly understood by those of ordinary skill in the art to which this disclosure belongs. It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims. Definitions of common terms in immunology, cellular and molecular biology can be found in The Merck Manual of Diagnosis and Therapy, 19th Edition, published by Merck Sharp & Dohme Corp., 2011 (ISBN 978-0-911910-19-3); Robert S. Porter et al. (eds.), The Encyclopedia of Molecular Cell Biology and Molecular Medicine, published by Blackwell Science Ltd., 1999-2012 (ISBN 9783527600908); and Robert A. Meyers (ed.), Molecular Biology and Biotechnology: a Comprehensive Desk Reference, published by VCH Publishers, Inc., 1995 (ISBN 1-56081-569-8); Immunology by Werner Luttmann, published by Elsevier, 2006; Janeway's Immunobiology, Kenneth Murphy, Allan Mowat, Casey Weaver (eds.), Taylor & Francis Limited, 2014 (ISBN 0815345305, 9780815345305); Lewin's Genes XI, published by Jones & Bartlett Publishers, 2014 (ISBN-1449659055); Michael Richard Green and Joseph Sambrook, Molecular Cloning: A Laboratory Manual, 4th ed., Cold Spring Harbor Laboratory Press, Cold Spring Harbor, N.Y., USA (2012) (ISBN 1936113414); Davis et al., Basic Methods in Molecular Biology, Elsevier Science Publishing, Inc., New York, USA (2012) (ISBN 044460149X); Laboratory Methods in Enzymology: DNA, Jon Lorsch (ed.) Elsevier, 2013 (ISBN 0124199542); Current Protocols in Molecular Biology (CPMB), Frederick M. Ausubel (ed.), John Wiley and Sons, 2014 (ISBN 047150338X, 9780471503385), Current Protocols in Protein Science (CPPS), John E. Coligan (ed.), John Wiley and Sons, Inc., 2005; and Current Protocols in Immunology (CPI) (John E. Coligan, A D A M Kruisbeek, David H Margulies, Ethan M Shevach, Warren Strobe, (eds.) John Wiley and Sons, Inc., 2003 (ISBN 0471142735, 9780471142737), the contents of which are all incorporated by reference herein in their entireties.

As used herein, the term "neuromuscular disorders" encompasses muscular dystrophies (including but not limited to severe or benign X-linked muscular dystrophy, limb-girdle dystrophy, facioscapulohumeral dystrophy, myotonic dystrophy, distal muscular dystrophy, progressive dystrophic ophthalmoplegia, oculopharyngeal dystrophy, Duchenne's muscular dystrophy, and Fukuyama-type congenital muscular dystophy); polymyositis; amyotrophic lateral sclerosis (ALS); muscle atrophy; muscle atrophy due to carpal tunnel syndrome; muscle wasting associated with congestive obstructive pulmonary disease; congenital myopathy; myotonia congenital; familial periodic paralysis; paroxysmal myoglobinuria; myasthenia gravis; Eaton-Lambert syndrome; secondary myasthenia; denervation atrophy; paroxymal muscle atrophy; muscle atrophy associated with cerebrovascular accidents (stroke), Parkinson's disease, multiple sclerosis, Huntington's (Huntington's chorea) and Creutzfeldt-Jakob disease; and sarcopenia, cachexia and other muscle wasting syndromes.

"Statins," "statin drugs," or "HMG-CoA reductase inhibitors", as used herein, refer to a class of drugs typically used to lower cholesterol levels by inhibiting the enzyme HMG-CoA reductase, which plays a central role in the production of cholesterol in the liver, and include, for example, lovastatin, simvastatin, pravastatin, atorvastatin, fluvastatin, rosuvastatin, cerivastatin, and pitavastatin.

As used herein, the term "lipophilic statin" or "poorly water-soluble statin" refers to a group of compounds that belong to the statin class of drugs, as defined herein, that typically have a solubility that is rated as "sparingly soluble", or lower, as that term is defined by the U.S. Pharmacopeia (2002) (p. 8), and includes, for example, simvastatin, cerivastatin, fluvastatin, lovastatin, pitavastatin, and atorvastatin, and stereoisomers thereof, and their pharmaceutically acceptable salts.

As used herein, a subject having a "cardiovascular disease" has any condition in which statins are typically used to reduce blood cholesterol levels including atherosclerosis, coronary heart disease (CHD), cerebrovascular disease, and peripheral vascular disease. Cardiovascular disorders are acute manifestations of CVD and include myocardial infarction, stroke, angina pectoris, transient ischemic attacks, and congestive heart failure. Cardiovascular disease, including atherosclerosis, usually results from the build-up of cholesterol, inflammatory cells, extracellular matrix and plaque. To be clear, a cardiovascular disease as used herein does not include any disease or disorder caused by deficiencies or issues with cardiac muscle function that are not secondary to problems with the cardiac vasculature.

As used herein, "familial hypercholesterolemia" (FH) refers to an autosomal dominant disorder that causes severe elevations in total cholesterol and low-density lipoprotein cholesterol (LDLc). The most common genetic defects in FH are LDLR mutations (prevalence 1 in 500, depending on the population), ApoB mutations (prevalence 1 in 1000), PCSK9 mutations (less than 1 in 2500) and LDLRAP1.

As used herein, a "therapeutically effective amount" or "effective amount" of a statin drug or formulation described herein is the minimum amount necessary to, for example, increase or improve one or more muscle function parameters, such as, for example, contractility, fatigue, and/or muscle damage.

As used herein, the term "comprising" means that other elements can also be present in addition to the defined elements presented. The use of "comprising" indicates inclusion rather than limitation.

As used herein the term "consisting essentially of" refers to those elements required for a given embodiment. The term permits the presence of additional elements that do not materially affect the basic and novel or functional characteristic(s) of that embodiment of the invention.

The term "consisting of" refers to compositions, methods, and respective components thereof as described herein, which are exclusive of any element not recited in that description of the embodiment.

Further, unless otherwise required by context, singular terms shall include pluralities and plural terms shall include the singular.

Other than in the operating examples, or where otherwise indicated, all numbers expressing quantities of ingredients or reaction conditions used herein should be understood as modified in all instances by the term "about." The term "about" when used in connection with percentages can mean±1%.

It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims.

All patents and other publications identified herein, both supra and infra, are expressly incorporated herein by reference for the purpose of describing and disclosing, for example, the methodologies described in such publications that could be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 9A. Myocardial Performance Index (MPI), a global measure of left ventricular function was measured by echocardiography. The first measurement was taken when mice were 12 months of age (Time, 0 weeks). One mdx group was then given Simvastatin for the remainder of the experiment (mdx Sim). WT Con mice were also used for this study. *$P<0.05$ and *$P<0.001$ versus mdx Con. FIG. 9B. Echocardiography was also used to measure diastolic function using the E'/A' ratio. Note that a ratio >1.0 is considered a normal value (dotted line). $P<0.01$ versus mdx Con. FIG. 9C. A representative Western blot showing the expression of Phospholamban phosphorylated at serine 16 (PLB S-16) and total Phospholamban (PLB) from cardiac muscle of old mice. FIG. 9D. Pooled data showing expression levels of PLB 5-16 and PLB from cardiac muscle of old mice (n≥6). *$P<0.05$ versus mdx Con, **$P<0.01$ versus WT Con. Data are shown as the mean±s.e.m.

FIG. 10A. Whole-body muscle damage was measured by the levels of plasma creatine kinase (CK) activity. *** $P<0.001$ for mdx Con (n=10) compared to mdx Sim (n=9). FIG. 10B. Representative H&E stained images of TA sections from mdx Con, mdx Sim, WT Con and WT Sim mice. Note the inflammatory cell infiltration in the mdx Con section. Scale bar=50 μm. FIG. 10C. Representative images (top) showing inflammation for mdx Con and mdx Sim using a CD68 antibody (green). The sarcolemma is labelled with a Caveolin-3 antibody (red). Scale bar=20 μm. Quantification of the CD68 levels for the two groups (n=9) is shown below (*$P<0.05$). FIG. 10D. Representative images (top) showing myosin heavy chain 2B (green), myosin heavy chain 2A (red) and myosin heavy chain 2x (unstained, black) in an mdx Con and mdx Sim muscle section. Pooled values for the percent of each fiber type are shown below for mdx Con (n=8) and mdx Sim (n=7) mice ($P<0.01$). Scale bar=200 μm. FIG. 10E. Diaphragm force normalized to cross-sectional area (specific force) was measured over a range of stimulation frequencies for mdx Con and mdx Sim mice. $P<0.01$ (n=9 for both groups). Insert shows representative specific force traces from an mdx Con and mdx Sim mouse, during stimulation at 120 Hz.

FIG. 11A. Representative traces showing specific force values during 120 Hz isometric contractions at the optimum muscle length for mdx and WT mice, with or without Simvastatin treatment. FIG. 11B. Pooled values of TA specific force for mdx Con (n=6), mdx Sim (n=6), WT Con (n=5) and WT Sim (n=5) mice. *$P<0.001$ compared to mdx Con, ### $P<0.001$ compared to both mdx groups. FIG. 11C. Representative Western blot showing NOX2 expression from TA (top right) and the pooled values for each group. Values were normalized to GAPDH, which was used as a loading control. $P<0.01$ compared to mdx Con, ***$P<0.001$ compared to mdx Con, ### $P<0.001$ compared to both mdx groups, ## $P<0.01$ compared to WT Con. FIG. 11D. Values for NOX2 expression plotted against TA specific force for mdx and WT mice with or without Simvastatin treatment. A linear regression line has been fitted to the data ($R^2$ adjusted=0.76, $P<0.001$).

FIG. 12A. Representative traces of TA muscle force for mdx and WT mice with or without Simvastatin treatment during 2 minutes of fatiguing contractions (every 2 seconds). FIG. 12B. Pooled values of TA force after 1 minute of fatigue. $P<0.01$ compared to mdx Con, *$P<0.001$ compared to mdx Con. FIG. 12C. Pooled values of TA force recovery after fatigue from 2 to 10 minutes. *$P<0.05$ for mdx Con versus all other groups, **$P<0.01$ for mdx Con versus all other groups.

FIG. 13A. Whole-body muscle damage in old mice was measured by the levels of plasma creatine kinase (CK) activity. *$P<0.05$ compared to mdx Con. FIG. 13B. Pooled specific force values of diaphragm muscle strips as measured at different stimulation frequencies for mdx Con and mdx Sim mice. *$P<0.05$, $P<0.01$ ($n\geq6$). FIG. 13C. Representative sections showing connective tissue levels in diaphragm muscles by fibronectin (green) immunostaining. The sarcolemma is outlined by Caveolin3 (red) and nuclei are stained with DAPI (blue). Scale bar=100 μm. FIG. 13D. Quantification of Fibronectin immunofluorescence from diaphragm muscle cross-sections. $P<0.01$ compared to mdx Con. FIG. 13E. Collagen I levels in homogenized diaphragm muscles were determined by the Hydroxyproline assay. *$P<0.05$ compared to mdx Con.

FIG. 14A. Western blot (top) showing the levels of the autophagy proteins LC3A (upper band) and LC3B (lower band) for mdx Con and mdx Sim. GAPDH is shown as a loading control. Pooled data (bottom) for LC3A and LC3B. **$P<0.01$ compared to mdx Con. FIG. 14B. Hydrogen peroxide ($H_2O_2$) levels in diaphragm muscle homogenates, as quantified with a fluorescent amplex red assay. *$P<0.05$ compared to mdx Con. FIG. 14C. Atrogin-1 mRNA levels in quadriceps muscles were quantified by qPCR and normalized to the internal control (HPRT). *$P<0.05$ compared to WT Con. **$P<0.01$ compared to WT Con.

DETAILED DESCRIPTION

Figure 1:
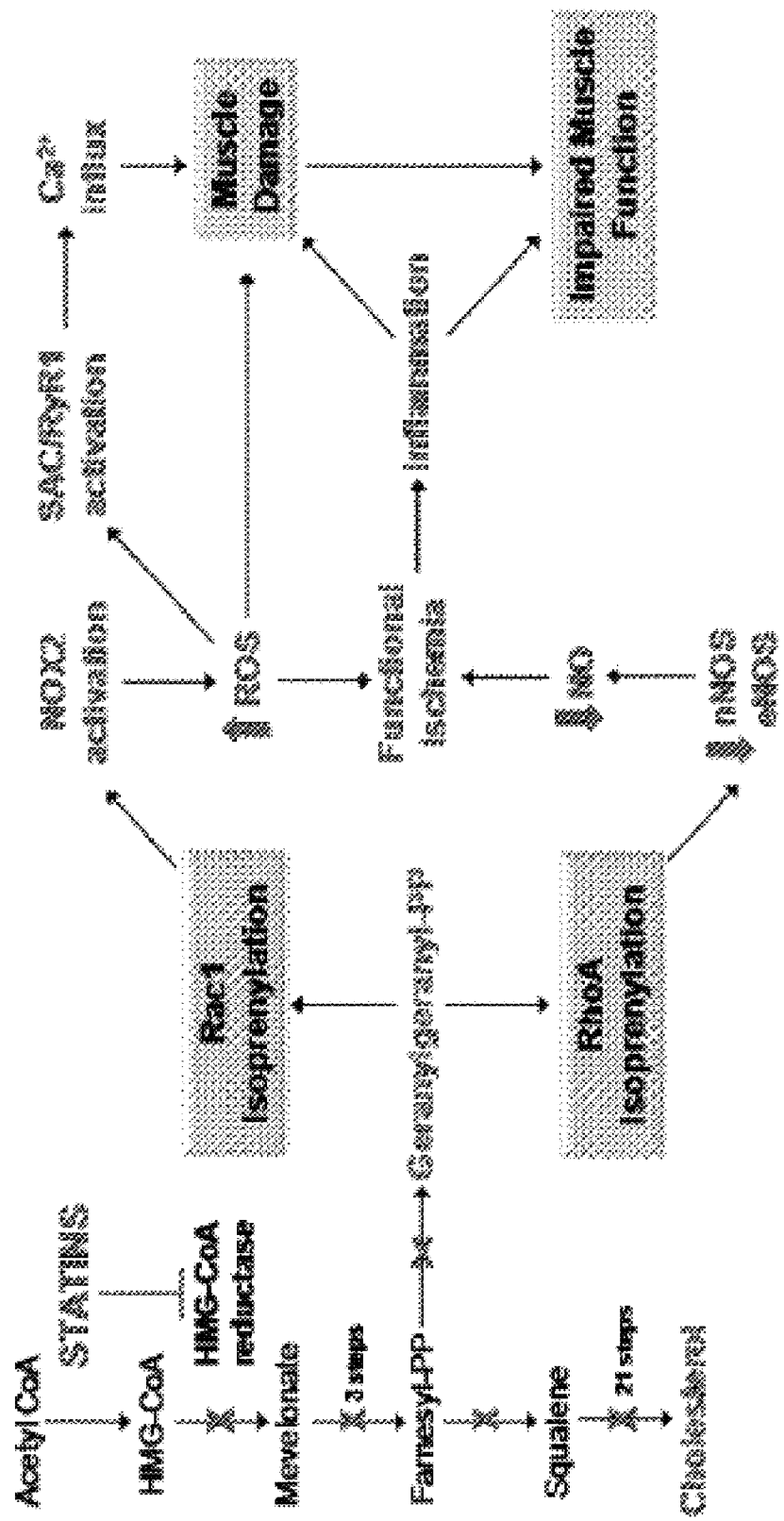
FIG. 1 shows an exemplary pathway by which statins improve dystrophic muscle health.
Figure 2A:
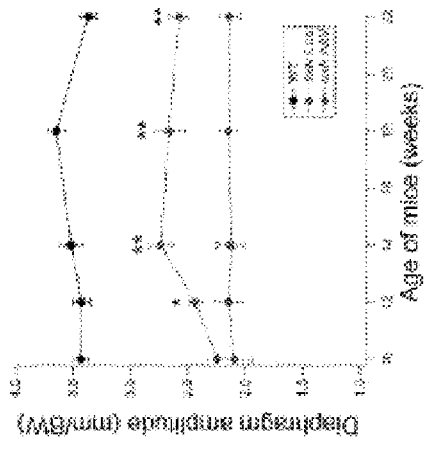
FIG. 2A shows an example of the diaphragm ultrasonography method, showing diaphragm movement during two inspiration-expiration contraction cylces. The measurement of the amplitude is shown for the first contraction.
Figure 2B:
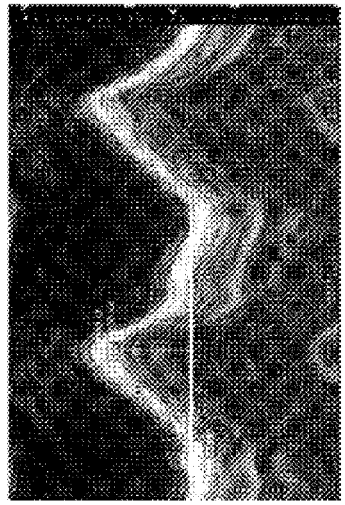
FIG. 2B shows that diaphragm ex vivo specific force and diaphragm in vivo amplitude are highly and significantly correlated for 8 and 18 month mdx mice.
Figure 2C:
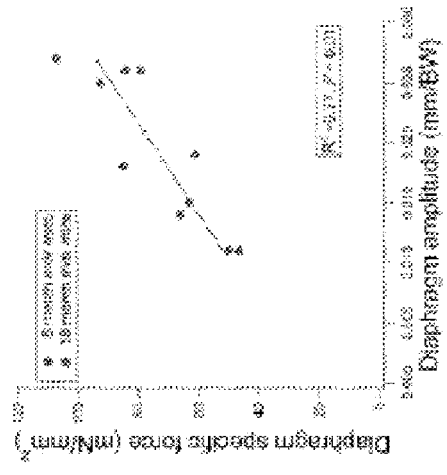
FIG. 2C shows a time-course of the change in diaphragm in vivo amplitude for WT mice, mdx control mice and mdx mice treated with micro-dystrophin AAV at 10 weeks of age.

Duchenne muscular dystrophy (DMD) is a lethal, degenerative muscle disease with no effective treatment. DMD muscle pathogenesis is characterized by chronic inflammation, oxidative stress and fibrosis. Statins, cholesterol lowering drugs, inhibit these deleterious processes in ischemic diseases affecting skeletal muscle. Statins have never been considered as a possible treatment for DMD or other muscular dystrophies principally because of the risk of skeletal muscle damage, a known side effect of statins. Herein, we show positive effects of administering statin drugs to dystrophic skeletal muscle. Simvastatin dramatically reduced damage and enhanced physiological function of both skeletal and cardiac muscle of dystrophic mdx mice, an animal model of DMD. Long-term simvastatin treatment vastly improved overall muscle health in mdx mice, reducing plasma CK activity, an established measure of muscle damage, to near normal levels. This was accompanied by reduced inflammation, more oxidative muscle fibers, and improved contractile force of the weak diaphragm muscle. Shorter-term treatment dramatically increased mdx hindlimb muscle force by 40%, protected against muscle fatigue, and increased mdx hindlimb muscle force by 40%, a value comparable to current dystrophin gene-based therapies. Increased force correlated with reduced NADPH Oxidase 2 protein expression, the major source of oxidative stress and contractile dysfunction in dystrophic muscle. Finally, in older, more severely dystrophic mdx mice with severe muscle degeneration, simvastatin decreased plasma CK activity, enhanced diaphragm force, and halved fibrosis, a major cause of functional decline in DMD. Moreover, Simvastatin reversed earlystage cardiac dysfunction, as evaluated by echocardiography. Improved cardiac function was associated with increased phosphorylation of phospholamban, a key regulatory protein of the Ca2+ pump (SERCA), a therapeutic target in DMD. These improvements were also accompanied by autophagy activation, a recent therapeutic target for DMD, and less oxidative stress. Together, the findings described herein demonstrate that statins, such as simvastatin, substantially improve the overall health and function of dystrophic skeletal muscles and provide an unexpected, novel, and affordable therapy for DMD and related neuromuscular diseases.

Statins

"Statins," "statin drugs," or "HMG-CoA reductase inhibitors", as used herein, refer to a class of drugs typically used to lower cholesterol levels by inhibiting the enzyme HMG-CoA reductase, which plays a central role in the production of cholesterol in the liver. Statins act by competitively inhibiting HMG-CoA reductase, the first committed enzyme of the cholesterol synthesis pathway. The interactions between statins and HMG-CoA reductase prevent the conversion of HMG-CoA to L-mevalonate resulting in the inhibition of the downstream cholesterol biosynthesis and numerous isoprenoid metabolites such as geranylgeranyl pyrophosphate (GGPP1) and farnesyl pyrophosphate (FPP). Statins are also known to exhibit a wide range of "cholesterol-independent" or "pleiotropic" effects that include, among others, improvement of endothelial function, inhibition of vascular inflammation and oxidation, and stabilizing of atherosclerotic plaques (Zhou and Liao, 2010) A variety of statins are produced by *Penicillium* and *Aspergillus* fungi as secondary metabolites.

Statins have been found to prevent cardiovascular disease and mortality in those who are at high risk. Known side effects of statins include muscle pain, increased risk of diabetes mellitus, and abnormalities in liver enzyme tests. Rare but severe adverse effects include muscle damage. In regard to muscle damage side effects associated with statin use, reported rare reactions include myopathies such as myositis (inflammation of the muscles) or even rhabdomyolysis (destruction of muscle cells), which can in turn result in life-threatening kidney injury. The risk of statin-induced rhabdomyolysis increases with older age, use of interacting medications, such as fibrates, and hypothyroidism. "Statin-induced myopathy" is a general term used to describe muscle pain or weakness with or without mildly raised CK levels in the blood caused by statin use. Some researchers have even suggested that hydrophilic statins, such as fluvastatin, rosuvastatin, and pravastatin, are less toxic than lipophilic statins, such as atorvastatin, lovastatin, and simvastatin (Hanai J et al. (2007). "The muscle-specific ubiquitin ligase atrogin-1/MAFbx mediates statin-induced muscle toxicity". J. Clin. Invest. 117 (12): 3940-51)). Thus, the results described herein in regard to the therapeutic efficacy of treatment of neuromuscular disorders, such as DMD, with statin drugs, are novel and unexpected.

The structural design of statins has been modeled to achieve different functionalities tightly related to each particular component of the molecule. The chemical structure of the statins is constituted by two components, the pharmacophore, which is a dihydroxyheptanoic acid segment, and its moiety composed of a ring system with different substituents. The function of the pharmacophore relies on the inhibition of the HMG-CoA reductase enzyme in a competitive, dose-dependent, and reversible manner. The stereoselectivity of the HMG-CoA reductase enzyme dictates the stereochemistry of the statins, which present two chiral carbon atoms, C3 and C5, on their pharmacophore. The moiety of the pharmacophore, according to the chemical modified ring systems and the nature of the substituents, generates the different structures of the statins. The ring system is a complex hydrophobic structure, covalently linked to the pharmacophore, which is involved in the binding interactions to the HMG-CoA reductase. The binding interactions of the ring are able to reduce the competition for the binding site between the statin and the endogenous HMG-CoA substrate because keeping the statin closed to the enzyme precludes the possibility of statin displacement by the endogenous substrate. The structure of the ring can be a partially reduced naphthalene (lovastatin, simvastatin, pravastatin), a pyrrole (atorvastatin), an indole (fluvastatin), a pyrimidine (rosuvastatin), a pyridine (cerivastatin), or a quinoline (pitavastatin).

The substituents on the rings define the solubility of the statins along with many of their pharmacological properties. Different substituents on the ring generate different structures. For instance, on the partially reduced naphthalene ring, as substituent, can be located a CH3 group and a 2-methylbutyrate ester (lovastatin), or a 2,2-methylbutyrate ester (simvastatin), which substantially increases the potency of the drug; on nitrogen containing rings, isopropyl and p-fluorophenyl substituents (atorvastatin and fluvastatin) can be attached.

Statins can be classified as fermentation-derived (also known as type 1, natural, or fungal-derived) statins or synthetic. Fermentation-derived statins include simvastatin (Zocor, Lipex, Simvastatin is a synthetic derivate of a fermentation product of *Aspergillus terreus*), lovastatin (Mevacor, Altoprev, Altocor), mevastatin (compactin), and pravastatin (Pravachol, Selektine, Lipostat). Fungal-derived statins exhibit close structural homology and were originally identified as secondary metabolites of fungi (Alberts, 1988). Mevastatin, one of the first identified, was isolated from *Penicillium citrinum* by Endo et al. (1976) and, in its active form, resembles the cholesterol precursor HMG-CoA. Subsequently, a more active fungal metabolite, mevinolin or lovastatin, was isolated from *Aspergillus terreus* by Alberts et al. (1980). Synthetic or type 2 statins include atorvastatin (Lipitor, Torvast), fluvastatin (Lescol, Lescol XL), pitavastatin (Livalo, Pitava), rosuvastatin (Crestor), and cerviastatin (Lipobay, Baycol, and withdrawn from the market in August, 2001 due to risk of serious rhabdomyolysis). Thus, in some embodiments of the methods described herein, a statin drug being administered is a natural statin drug. In some embodiments of the methods described herein, a statin drug being administered is a synthetic statin drug.

The functional difference between natural and synthetic statins relies on their ability to interact and inhibit the HMG-CoA reductase and on their lipophilicity. Type 2 statins are known to form more interactions with HMG-CoA reductase because of their structural characteristics; for instance, atorvastatin and rosuvastatin have additional hydrogen binding interactions. Indeed, rosuvastatin also exhibits a polar interaction between the methane sulfonamide group and the HMG-CoA reductase enzyme. These structural properties render this statin the most efficient in terms of dose able to reduce HMG-CoA reductase activity by 50% (Davidson, 2002).

Pharmacokinetic properties of the statins are orchestrated by several factors, including their active or lactone form, their lipophilic/hydrophilic rate, and their absorption and metabolism. Statins are typically administrated orally as active hydroxy acids, except for lovastatin and simvastatin, which are administrated as lactone prodrugs and then hydrolyzed to hydroxy acid form (Corsini et al., 1995). The percentage of absorption of statin drugs is between 30 and 98% and the time to reach peak plasma concentration (Tmax) is within 4 h after administration. The daily absorption of a given statin drug can vary according to the time of administration and food intake; for instance, changes in lipid and apolipoprotein values are similar after morning and evening administration of atorvastatin. Rate and extent of equivalent absorption of atorvastatin were lower during evening than morning. When consumed with food, lovastatin is more efficiently absorbed with respect to fluvastatin, atorvastatin, and pravastatin, which have a reduced absorption, whereas absorption of rosuvastatin, simvastatin, and cerivastatin is not affected by food consumption. Pharmacological Actions of Statins: A Critical Appraisal in the Management of Cancer, Pharmacol Rev 64:102-146, 2012, the contents of which are herein incorporated by reference in their entireties.

Statins can also be classified based on their solubility in water as "hydrophilic" (i.e., water loving or lipophobic) or "lipophilic" (i.e., water hating or hydrophobic). Some statins are poorly soluble in water, but soluble in lipids, and vice versa. The solubility profile of a statin is a fundamental characteristic that governs the hepatoselectivity of the statins and their inhibitory effect on HMG-CoA reductase. Likewise, the solubility profile affects the degree to which statins are available to muscle tissues. Lipophilic statins enter cells by passive diffusion, whereas hydrophilic statin uptake is carrier-mediated. Lipophilic statins show an efficient activity at both hepatic and extrahepatic sites, whereas hydrophilic statins are more hepatoselective (Pharmacol Rev 64:102-146, 2012). As used herein, the term "lipophilic statin" or "poorly water-soluble statin" refers to a group of compounds that belong to the statin class of drugs, as defined herein, that typically have a solubility that is rated as "sparingly soluble", or lower, as that term is defined by the U.S. Pharmacopeia (2002) (p. 8). The U.S. Pharmacopeia defines several such levels of solubility as follows: "sparingly soluble" refers to an aqueous solubility that ranges from about 1/30 to about 1/100 (mg/ml); "slightly soluble" refers to an aqueous solubility that ranges from about 1/100 to about 1/1,000 (mg/ml); "very slightly soluble" refers to an aqueous solubility that ranges from about 1/1,000 to about 1/10,000 (mg/ml); and "practically insoluble, or insoluble" refers to an aqueous solubility that is 1/10,000 (mg/ml) or less. The phrase "poorly water-soluble statin" also includes any pharmaceutically acceptable salts, or stereoisomers, of a poorly water-soluble statin. Lipophilic or poorly water-soluble statins include, for example, simvastatin, cerivastatin, fluvastatin, lovastatin, pitavastatin, and atorvastatin, and stereoisomers thereof, and their pharmaceutically acceptable salts. Simvastatin is presently the most lipophilic statin drug approved for use in humans. Generally speaking, a statin or statin derivative is lipophilic if its water solubility is within 10% of the water solubility of any of simvastatin, cerivastatin, fluvastatin, lovastatin, pitavastatin, and atorvastatin. Hydrophilic or water-soluble statins include, for example, pravastatin and rosuvastatin. The lipophilic properties of the statins are accompanied, except for pitavastatin, by low systemic bioavailability because of an extensive first-pass effect at the hepatic level (Garcia et al., 2003). Statins' lipophilicity enables them to passively penetrate the cells of extrahepatic tissues. In some embodiments of the methods described herein, a statin drug being administered is a lipophilic statin drug selected from simvastatin, atorvastatin, cerivastatin, fluvastatin, lovastatin, and pitavastatin, and their pharmaceutically acceptable salts and stereoisomers.

Statins can also be classified based on their stability under acidic conditions. Some statins are stable under acidic conditions. As used herein, the phrase "acid-stable statin" refers to a group of compounds that belong to the statin class of drugs and do not substantially degrade or undergo conversion to metabolites under acidic conditions. For example, acid-stable statins are those where less than about 25% of the compound is degraded or converted to metabolites in an environment with a pH of less than about 4. For example, an acid-stable statin can be a statin where about 20% of the compound is degraded in an environment with a pH of less than about 4, where about 15% of the compound is degraded in an environment with a pH of less than about 4, where about 10% of the compound is degraded in an environment with a pH of less than about 4, or where about 5% or less of the compound is degraded in an environment with a pH of less than about 4. The phrase "acid-stable statin" also includes any pharmaceutically acceptable salts or stereoisomers, of an acid-stable statin. Examples of acid-stable statins include simvastatin, lovastatin, fluvastatin, atorvastatin, and rosuvastatin, and their pharmaceutically acceptable salts and stereoisomers. In some embodiments of the methods described herein, a statin drug being administered is an acid-stable statin drug selected from simvastatin, lovastatin, fluvastatin, atorvastatin, and rosuvastatin, and their pharmaceutically acceptable salts and stereoisomers.

Statins can also be classified based on their molecular weight. For example, due to their large molecular size, some statins are poorly diffusively permeable through lipid membranes. As used herein, the term "large molecular weight statin" refers to any statin with a molecular weight of greater than about 475 Daltons. For example, large molecular weight statins include statins with molecular weights of greater than about 475, greater than about 500, greater than about 600, greater than about 700, greater than about 800, greater than about 900, or greater than about 1000 Daltons. The phrase "large molecular weight statin" also includes any pharmaceutically acceptable salts, and any stereoisomers, of a large molecular weight statin. Examples of large molecular weight statins include atorvastatin and rosuvastatin, and stereoisomers thereof, and their pharmaceutically acceptable salts. In some embodiments of the methods described herein, a statin drug being administered is not a large molecular weight statin.

One of ordinary skill in the art will appreciate that the statin characteristics and properties discussed herein are not mutually exclusive and that a given statin can have one or more of these properties. For example, as used herein, the term "acid-stable, lipophilic" refers to a statin that has the characteristics of an acid-stable statin and is also a lipophilic statin, as these terms are used herein. An example of an acid-stable and lipophilic statin is simvastatin as well as its pharmaceutically acceptable salts, and any stereoisomers.

Statin Formulations and Administration

For administration to a subject in need thereof, e.g., a subject diagnosed with or predisposed to a neuromuscular disorder, the statin drug can be provided in a pharmaceutically acceptable composition. As used herein, the term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The pharmaceutically acceptable composition used to administer a statin can further comprise one or more pharmaceutically acceptable carriers and/or diluents. As used herein "pharmaceutically acceptable carrier and/or diluent" includes any and all solvents, dispersion media, coatings, antibacterial and antifungal agents, isotonic and absorption delaying agents and the like that are pharmaceutically acceptable as the term is defined above. Except insofar as any conventional media or agent is incompatible with the active ingredient, use thereof in the therapeutic compositions is contemplated. Supplementary active ingredients can also be incorporated into the compositions.

Some examples of materials which can serve as pharmaceutically-acceptable carriers include, but are not limited to, gelatin, buffering agents, such as magnesium hydroxide and aluminum hydroxide, pyrogen-free water, isotonic saline, Ringer's solution, pH buffered solutions, bulking agents such as polypeptides and amino acids, serum components, such as serum albumin, HDL and LDL, and other non-toxic compatible substances employed in pharmaceutical formulations. Preservatives and antioxidants can also be present in the formulation. The terms such as "excipient", "carrier", "pharmaceutically acceptable carrier" or the like are used interchangeably herein.

Pharmaceutically acceptable carriers can vary in a therapeutic composition as described herein, depending on the formulation and/or administration route, as known in the art. Such formulations and dosages of statins are discussed in, for example, United States Patent Applications 20150164893, 20150065553, 20120270933, and 20110027371, the contents of each of which are herein incorporated by reference in their entireties.

In some embodiments, a statin drug is administered as a modified-release or controlled-release formulation comprising a therapeutically effective amount of at least one statin, or a pharmaceutically acceptable salt thereof. A modified or controlled release formulation changes the kinetics of release as a bioavailable form from the dosage form administered. A modified or controlled-release formulation can extend the influence or effect of a therapeutically effective dose of an active compound in a patient. In addition to maintaining therapeutic levels of the active compound, a modified or controlled-release formulation can also be designed to delay the release of the active compound for a specified period or until the dosage form has arrived at or left a given site, e.g., leaving the stomach and arriving in the different environment of the intestine.

Modified or controlled-release formulations also provide advantages in that equivalent, or higher, doses of statins can be used, with better efficacy and/or fewer side effects observed. Because the statins used in the described methods, in some embodiments, are stable under acidic conditions, the compositions do not require a protective coating to avoid conversion of the statin in the stomach to metabolites prior to absorption in the intestine. Although not required, in some embodiments such protective coatings can nevertheless be used if a delayed release is desired. The option of using, or not using, a protective coating is desirable because it allows a greater degree of flexibility in designing modified or controlled-release formulations that release the statin at the desired rate.

While lipophilic statins are generally more likely to be available to non-hepatic tissues, in some embodiments of the methods described herein, modified or controlled-release formulations comprising a therapeutically effective amount of a statin, such as a lipophilic statin, or a pharmaceutically acceptable salt thereof, are designed to increase the solubility of the statin. Improving the solubility of a lipophilic or poorly water-soluble statin can be achieved using several methods. As used herein, the term "solubility improving method" refers to any method that, when used as part of the formulation, improves the solubility of a poorly water-soluble statin by at least one level of solubility as defined in the U.S. Pharmacopeia (2002). For example, in one embodiment the solubility is improved from "slightly soluble" to "sparingly soluble." In another embodiment, the solubility is improved from "very slightly soluble" to "slightly soluble". In a further embodiment, the solubility is improved from "practically insoluble, or insoluble" to "very slightly soluble." In some embodiments, the solubility of the poorly water-soluble statin can be improved by micronization. This is accomplished by conventional micronization techniques known to those of skill in the art, for example, jet milling, air jet milling, impact milling, media milling (aqueous or solvent), ball milling, pin milling, or fluid bed milling. In some embodiments, about 90% of the drug particles are less than about 20 microns in size. In some embodiments, about 50% of the drug particles are not more than about 10 microns in size. In some embodiments, particles of the poorly water-soluble statin are prepared as an even smaller, e.g., sub-micron, or nanoparticle sizes.

Additionally, excipients can be included in the formulation to enhance the solubility/dissolution of the poorly water-soluble statin drugs. For example, surfactants, detergents, or any other agents that improve the dissolution of the statins can be included in the formulation. Such surfactants include, but are not limited to, sodium lauryl sulphate. The formulations also contemplate incorporation of suitable excipients to maintain the integrity of particles of the active ingredient.

It is also contemplated that water-soluble statins can be modified in some embodiments to make them more lipophilic. This can be, for example, by chemically derivatizing the statin, or by formulating with one or more agents that modify its lipophilic character. Thus, in some embodiments of the methods described herein, modified-release formulations can be administered that comprise a therapeutically effective amount of a statin, or a pharmaceutically acceptable salt thereof, where the membrane permeability of the statin is improved by the addition of an enhancing agent. Such formulations where the permeability of the statin is improved can increase its overall bioavailibility. As used herein, the term "membrane permeability enhancer" refers to any agent that improves the membrane permeability of a statin. Enhancing agents that can be used to increase membrane permeability include, but are not limited to, medium chain fatty acids, such as six-carbon to twenty-carbon fatty acids, and in particular the eight- and ten-carbon forms, such as sodium caprate. Such agents include, but are not limited to, fatty acids, fatty acid esters, and fatty alcohols. Such compounds can be hydrophobic or have limited water solubility, and the compounds may have a molecular weight of from about 150 to about 300 Daltons. Fatty alcohols include, but are not limited to, stearyl alcohol, and oleyl alcohol. Fatty acids include, but are not limited to, oleic acid, lauric acid, myristic acid, palmitic acid, stearic acid, linoleic acid, capric acid, monoglycerides, diglycerides, acylcholines, caprylic acids, acylcarnitines, sodium caprate, and palmitoleic acid. Fatty acid esters containing more than 10 to 12 carbons can also be used. Examples of fatty acid esters include, but are not limited to, isopropyl myristate and methyl and ethyl esters of oleic and lauric acid.

Ionic enhancers can also be used, in some embodiments. Examples of ionic enhancers that can be used include, but are not limited to, sodium lauryl sulfate, sodium laurate, polyoxyethylene 20-cetylether, laureth-9, sodium dodecylsulfate, and dioctyl sodium sulfosuccinate.

Bile salts can also be used, in some embodiments. Examples of bile salts that can be used include, but are not limited to, sodium glycocholate, sodium deoxycholate, sodium taurocholate, sodium taurodihydrofusidate, and sodium glycodihydrofusidate.

Chelating agents can be used, in some embodiments. Examples of chelating agents that can be used include, but are not limited to, ethylenediamine tetra-acetic acid (EDTA), citric acid, and salicylates.

Another group of enhancers that can be used, in some embodiments, includes low molecular weight alcohols. Such alcohols can have a molecular weight of less than about 200 Daltons, or less than about 150 Daltons, or less than about 100 Daltons. They can also be hydrophilic, having greater than about 2 wt %, about 5 wt %, or about 10 wt % solubility in water at room temperature. Examples of such alcohols include, but are not limited to, methanol, ethanol, propanol, isopropanol, butanol, benzyl alcohol, glycerin, polyethylene glycol, propanediol, and propylene glycol.

Sulfoxides can also be used, in some embodiments. Examples of sulfoxides include, but are not limited to, dimethyl sulfoxide and decmethyl sulfoxide.

Other enhancers that can be used, in some embodiments, include urea and its derivatives, unsaturated cyclic ureas, 1-dodecylazacycloheptan-2-one, cyclodextrin, enamine derivatives, terpenes, liposomes, acyl carnitines, cholines, peptides (including polyarginine sequences or arginine rich sequences), peptidomimetics, diethyl hexyl phthalate, octyldodecyl myristate, isostearyl isostearate, caprylic/capric triglyceride, glyceryl oleate, and various oils (such as wintergreen or eucalyptol).

The pharmaceutical compositions comprising a statin drug used in the methods described herein can be formulated into a dosage form that modifies the release of the statin. Examples of suitable modified or controlled-release formulations that can be used in accordance with the methods described herein include, but are not limited to, matrix systems, osmotic pumps, and membrane controlled dosage forms. These formulations can be single-unit or multi-unit compositions.

In some embodiments, the modified or controlled-release formulations comprising a statin drug are provided as matrix-based dosage forms. Matrix formulations according to the invention can include hydrophilic, e.g., water-soluble, and/or hydrophobic, e.g., water-insoluble, polymers. The matrix formulations of the present invention can optionally be prepared with functional coatings, which can be enteric, e.g., exhibiting a pH-dependent solubility, or non-enteric, e.g., exhibiting a pH-independent solubility.

Matrix formulations comprising a statin drug can be prepared by using, for example, direct compression or wet granulation. A functional coating, as noted above, can then be applied in accordance with the invention. Additionally, a barrier or sealant coat can be applied over a matrix tablet core prior to application of a functional coating. The barrier or sealant coat can serve the purpose of separating an active ingredient from a functional coating, which can interact with the active ingredient, or it can prevent moisture from contacting the active ingredient. Details of barriers and sealants are provided below.

In some embodiments, statin and optional pharmaceutically acceptable excipient(s) are dispersed within a polymeric matrix, which typically comprises one or more water-soluble polymers and/or one or more water-insoluble polymers. The drug can be released from the dosage form by diffusion and/or erosion. Suitable water-soluble polymers include, but are not limited to, polyvinyl alcohol, polyvinylpyrrolidone, methylcellulose, hydroxypropylcellulose, hydroxypropylmethyl cellulose, or polyethylene glycol, and/or mixtures thereof. Suitable water-insoluble polymers include, but are not limited to, ethylcellulose, cellulose acetate, cellulose propionate, cellulose acetate propionate, cellulose acetate butyrate, cellulose acetate phthalate, cellulose triacetate, poly(methyl methacrylate), poly(ethyl methacrylate), poly(butyl methacrylate), poly(isobutyl methacrylate), poly(hexyl methacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate), poly(ethylene), poly(ethylene) low density, poly(ethylene) high density, poly(ethylene oxide), poly(ethylene terephthalate), poly (vinyl isobutyl ether), poly(vinyl acetate), poly(vinyl chloride), or polyurethane, and/or mixtures thereof.

In some embodiments, the modified-release formulations comprising a statin drug are provided as osmotic pump dosage forms. Osmotic pumps are well known in the art. For example, U.S. Pat. Nos. 4,088,864, 4,200,098, and 5,573,776, each of which is hereby incorporated by reference for this purpose, describe osmotic pumps and methods of their manufacture. In an osmotic pump dosage form, a core containing the statin and optionally one or more osmotic excipients is typically encased by a selectively permeable membrane having at least one orifice. The selectively permeable membrane is generally permeable to water, but impermeable to the drug. When the system is exposed to body fluids, water penetrates through the selectively permeable membrane into the core containing the drug and optional osmotic excipients. The osmotic pressure increases within the dosage form. Consequently, the drug is released through the orifice(s) in an attempt to equalize the osmotic pressure across the selectively permeable membrane.

In more complex pumps, the dosage form can contain two internal compartments in the core. The first compartment contains the drug and the second compartment can contain a polymer, which swells on contact with aqueous fluid. After ingestion, this polymer swells into the drug-containing compartment, diminishing the volume occupied by the drug, thereby delivering the drug from the device at a controlled rate over an extended period of time. Such dosage forms are often used when a zero order release profile is desired.

Typical materials for the selectively permeable membrane include selectively permeable polymers known in the art to be useful in osmosis and reverse osmosis membranes, such as cellulose acylate, cellulose diacylate, cellulose triacylate, cellulose acetate, cellulose diacetate, cellulose triacetate, agar acetate, amylose triacetate, beta glucan acetate, acetaldehyde dimethyl acetate, cellulose acetate ethyl carbamate, polyamides, polyurethanes, sulfonated polystyrenes, cellulose acetate phthalate, cellulose acetate methyl carbamate, cellulose acetate succinate, cellulose acetate dimethyl aminoacetate, cellulose acetate ethyl carbamate, cellulose acetate chloracetate, cellulose dipalmitate, cellulose dioctanoate, cellulose dicaprylate, cellulose dipentanlate, cellulose acetate valerate, cellulose acetate succinate, cellulose propionate succinate, methyl cellulose, cellulose acetate p-toluene sulfonate, cellulose acetate butyrate, lightly cross-linked polystyrene derivatives, cross-linked poly(sodium styrene sulfonate), poly(vinylbenzyltrimethyl ammonium chloride), and/or mixtures thereof.

The osmotic agents that can be used in the pump are typically soluble in the fluid that enters the device following administration, resulting in an osmotic pressure gradient across the selectively permeable wall against the exterior fluid. Suitable osmotic agents include, but are not limited to, magnesium sulfate, calcium sulfate, magnesium chloride, sodium chloride, lithium chloride, potassium sulfate, sodium carbonate, sodium sulfite, lithium sulfate, potassium chloride, sodium sulfate, d-mannitol, urea, sorbitol, inositol, raffinose, sucrose, glucose, hydrophilic polymers such as cellulose polymers, and/or mixtures thereof.

As discussed above, the osmotic pump dosage form of a statin drug can contain a second compartment containing a swellable polymer. Suitable swellable polymers typically interact with water and/or aqueous biological fluids, which causes them to swell or expand to an equilibrium state. Acceptable polymers exhibit the ability to swell in water and/or aqueous biological fluids, retaining a significant portion of such imbibed fluids within their polymeric structure, so as to increase the hydrostatic pressure within the dosage form. The polymers can swell or expand to a very high degree, usually exhibiting a 2- to 50-fold volume increase. The polymers can be non-cross-linked or cross-linked. In one embodiment, the swellable polymers are hydrophilic polymers. Suitable polymers include, but are not limited to, poly(hydroxy alkyl methacrylate) having a molecular weight of from about 30,000 to about 5,000,000; kappa-carrageenan; polyvinylpyrrolidone having a molecular weight of from about 10,000 to about 360,000; anionic and cationic hydrogels; polyelectrolyte complexes; poly (vinyl alcohol) having low amounts of acetate, cross-linked with glyoxal, formaldehyde, or glutaraldehyde, and having a degree of polymerization from about 200 to about 30,000; a mixture including methyl cellulose, cross-linked agar and carboxymethyl cellulose; a water-insoluble, water-swellable copolymer produced by forming a dispersion of finely divided maleic anhydride with styrene, ethylene, propylene, butylene, or isobutylene; water-swellable polymers of N-vinyl lactams; and/or mixtures of any of the foregoing.

In some embodiments of the methods described herein, the modified-release formulations of a statin drug can also be provided as membrane-controlled formulations. Membrane-controlled formulations of the present invention can be made by preparing a rapid release core, which may be a monolithic (e.g., tablet) or multi-unit (e.g., pellet) type, and coating the core with a membrane. The membrane-controlled core can then be further coated with a functional coating. In between the membrane-controlled core and the functional coating, a barrier or sealant can be applied. The barrier or sealant can alternatively, or additionally, be provided between the rapid release core and the membrane coating.

In some embodiments, statins are provided in multiparticulate membrane-controlled formulations. The membrane coating can comprise a polymeric material comprising a major proportion (i.e., greater than 50% of the total polymeric content) of one or more pharmaceutically acceptable water-soluble polymers, and optionally a minor proportion (i.e., less than 50% of the total polymeric content) of one or more pharmaceutically acceptable water-insoluble polymers. Alternatively, the membrane coating can comprise a polymeric material comprising a major proportion (i.e., greater than 50% of the total polymeric content) of one or more pharmaceutically acceptable water-insoluble polymers, and optionally a minor proportion (i.e., less than 50% of the total polymeric content) of one or more pharmaceutically acceptable water-soluble polymers.

The coating membrane can further comprise one or more soluble excipients so as to increase the permeability of the polymeric material. Suitably, the soluble excipient is selected from among a soluble polymer, a surfactant, an alkali metal salt, an organic acid, a sugar, and a sugar alcohol. Such soluble excipients include, but are not limited to, polyvinyl pyrrolidone, polyethylene glycol, sodium chloride, surfactants such as sodium lauryl sulfate and polysorbates, organic acids such as acetic acid, adipic acid, citric acid, fumaric acid, glutaric acid, malic acid, succinic acid, and tartaric acid, sugars such as dextrose, fructose, glucose, lactose, and sucrose, sugar alcohols such as lactitol, maltitol, mannitol, sorbitol, and xylitol, xanthan gum, dextrins, and maltodextrins. In some embodiments, polyvinyl pyrrolidone, mannitol, and/or polyethylene glycol can be used as soluble excipients. The soluble excipient(s) can be used in an amount of from about 1% to about 10% by weight, based on the total dry weight of the polymer.

In some embodiments, the polymeric material comprises one or more water-insoluble polymers, which are also insoluble in gastrointestinal fluids, and one or more water-soluble pore-forming compounds. For example, the water-insoluble polymer can comprise a terpolymer of polyvinylchloride, polyvinylacetate, and/or polyvinylalcohol. Suitable water-soluble pore-forming compounds include, but are not limited to, saccharose, sodium chloride, potassium chloride, polyvinylpyrrolidone, and/or polyethyleneglycol. The pore-forming compounds can be uniformly or randomly distributed throughout the water insoluble polymer. Typically, the pore-forming compounds comprise about 1 part to about 35 parts for each about 1 to about 10 parts of the water-insoluble polymers.

The coating membranes, and functional coatings as well, can also include a material that improves the processing of the polymers. Such materials are generally referred to as plasticizers and include, for example, adipates, azelates, benzoates, citrates, isoebucates, phthalates, sebacates, stearates and glycols. Representative plasticizers include acetylated monoglycerides, butyl phthalyl butyl glycolate, dibutyl tartrate, diethyl phthalate, dimethyl phthalate, ethyl phthalyl ethyl glycolate, glycerin, ethylene glycol, propylene glycol, triacetin citrate, triacetin, tripropinoin, diacetin, dibutyl phthalate, acetyl monoglyceride, polyethylene glycols, castor oil, triethyl citrate, polyhydric alcohols, acetate esters, gylcerol triacetate, acetyl triethyl citrate, dibenzyl phthalate, dihexyl phthalate, butyl octyl phthalate, diisononyl phthalate, butyl octyl phthalate, dioctyl azelate, epoxidised tallate, triisoctyl trimellitate, diethylhexyl phthalate, di-n-octyl phthalate, di-i-octyl phthalate, di-i-decyl phthalate, di-n-undecyl phthalate, di-n-tridecyl phthalate, tri-2-ethylhexyl trimellitate, di-2-ethylhexyl adipate, di-2-ethylhexyl sebacate, di-2-ethylhexyl azelate, dibutyl sebacate, glyceryl monocaprylate, and glyceryl monocaprate. In one embodiment, the plasticizer is dibutyl sebacate. The amount of plasticizer used in the polymeric material typically ranges from about 10% to about 50%, for example, about 10, 20, 30, 40, or 50%, based on the weight of the dry polymer.

In some embodiments, an oral dosage form containing a multiparticulate statin formulation is provided in the form of caplets, capsules, particles for suspension prior to dosing, sachets, films, or tablets. When the dosage form is in the form of tablets, the tablets can be, in some embodiments, chewable tablets, disintegrating tablets, fast or rapidly dissolving tablets, effervescent tablets, fast melt tablets, and/or mini-tablets. The dosage form can be of any shape suitable for oral administration of a drug, such as spheroidal, cube-shaped oval, or ellipsoidal. In some embodiments, an oral dosage form containing a multiparticulate statin formulation is provided in the form of a rapidly dissolving film. Rapidly dissolving films for oral administration are described, e.g., in U.S. Pat. No. 6,419,903 and international application No. WO2003030883, both of which are incorporated herein by reference. The dosage forms can be prepared from the multiparticulates in a manner known in the art and include additional pharmaceutically acceptable excipients, as desired. Methods of producing active drug formulations in the form of caplets, capsules, particles for suspension prior to dosing, sachets, films, or tablets are known in the art.

The formulations of statin drugs can also be prepared as liquids, which can be filled into soft gelatin capsules. For example, the liquid can include a solution, suspension, emulsion, microemulsion, precipitate, or any other desired liquid media carrying the statin(s). The liquid can be designed to improve the solubility of the statin(s) upon release, or can be designed to form a drug-containing emulsion or dispersed phase upon release. Examples of such techniques are well known in the art. Soft gelatin capsules can be coated, as desired, with a functional coating to delay the release of the drug.

All of the particular embodiments described herein, including but not limited to, matrix-based, osmotic pump-based, soft gelatin capsules, and/or membrane-controlled forms, which may further take the form of monolithic and/or multi-unit dosage forms, can have a functional coating. Such coatings generally serve the purpose of delaying the release of the drug for a predetermined period. For example, such coatings may allow the dosage form to pass through the stomach without being subjected to stomach acid or digestive juices. For the acid-stable statins used in formulations described herein, such protective coatings are not required, but can be used as another way to control the time and place of drug delivery. Thus, such coatings can dissolve or erode upon reaching a desired point in the gastrointestinal tract, such as the upper intestine.

Such functional coatings can exhibit pH-dependent (enteric) or pH-independent (non-enteric) solubility profiles. Those with pH-independent profiles generally erode or dissolve away after a predetermined period, and the period is generally related to the thickness and composition of the coating. Those with pH-dependent profiles, on the other hand, can maintain their integrity while in the acid pH of the stomach, but quickly erode or dissolve upon entering the more basic upper intestine.

Thus, a matrix-based, osmotic pump-based, and/or membrane-controlled formulation can be further coated with a functional coating that delays the release of the drug. For example, a membrane-controlled formulation can be coated with an enteric coating that delays the exposure of the membrane-controlled formulation until the upper intestine is reached. Examples of functional coatings such as these are well known to those in the art.

In some embodiments, the statin formulations initially delay the release of the drug. Following the delay, the formulation can rapidly release the drug. Such formulations would provide a more rapid and/or immediate therapeutic effect for the subject.

Formulations for use in the methods described herein can further comprise pH-modifying agents, for example, agents exhibiting a pKa of from about 1 to about 6.5. Such agents include, but are not limited to, dicarboxylic acids. Dicarboxylic acids include, but are not limited to, 2-ethandioic (oxalic), 3-propandioic (malonic), 4-butandioic (succinic), 5-pentandioic (glutaric), 6-hexandioic (adipic), cis-butenedioic (maleic), trans-butenedioic (fumaric), 2,3-dihydroxybutandioic (tartaric), 2-hydroxy-1,2,3-propanetic carboxylic (citric), pimelic, suberic, azelaic, and sebacic acids. In some embodiments, one or more dicarboxylic acids are included in the formulation.

In some embodiments, a statin drug is administered as a liquid formulation. Liquid formulations of orally administered drugs can be preferred when a subject cannot physically swallow a tablet or a pill, for example, or is a subject younger than 10 years of age, for example. Accordingly, liquid formulations are useful for treating children, adolescents, and other individuals to whom tablet or capsule formulations are difficult or impractical to administer or whose dosage is not available in solid form and should be individualized. Typical liquid formulations for use with the methods described herein comprise about 0.05-10% weight to weight (w/w) of a statin, such as simvastatin, or a combination of statins. Preferred formulations have 0.05-2.5% w/w of statin, and more preferred liquid formulations have about 0.2% w/w statin. Alternatively, the amount of statin in a formulation can be expressed in mg/ml. Liquid formulations can comprise about 0.01-25 mg/ml of statin, preferably formulations include 1-5 mg/ml of statin, more preferably formulations include about 2-5 mg/ml of statin. Higher concentrations can be desirable so that volume/dose can be reduced. The total amount of statin in a formulation can be due to a single statin or a combination of statins. To be clear, combinations of statins are contemplated for both liquid and non-liquid formulations. Exemplary descriptions of liquid statin formulations are provided in United States Patent Application 20120270933, the contents of which are herein incorporated by reference in their entireties.

Liquid statin formulations also include a vehicle (i.e. a solubilizer or solubilizing agent) to solubilize the statin. While many solubilizers are known to those of skill in the art, data show that certain vehicles, or combinations thereof, are more suitable than others. It is envisioned that liquid formulations can include one or more of the following vehicles: propylene glycol, minerals, propylene glycol-monostearate, propylene glycol alginate, natural glycerine, niacin, synthetic glycerine, vitamins, sorbitol, alcohols, myristyl alcohol, carboxymethylcellulose, labrasol, copovidone, Captex 355, croscarmellose sodium, polyethylene glycol (PEG) 400, PEG 1000, PEG 1450, PEG 1540, crospovidone, ethyl cellulose, aqueous polysorbate 20, aqueous polysorbate 40, aqueous polysorbate 60, aqueous polysorbate 80, cellulose, oxidized cellulose, polyoxyl 10 oleoyl ether, cellulose sodium phosphate, polyoxyl 20 cetostearyl, hyopromellose, poloyxyl 35 castor oil, polyoxyl 40 hydrogentated castor oil, polyoxyl 40 stearate, poloxyl lauryl ether, poloxyl oleate, poloxyl stearyl ether, or any combination thereof. Preferred vehicles include propylene glycol, polyethylene glycol, PEG 400, glycerine, and combinations of glycerine with either propylene glycol or polyethylene glycols of various molecular weights.

Preferred embodiments of oral statin liquid solutions can also include an antioxidant, flavoring, preservative, or a combination thereof. More preferably, oral solutions include all three elements (i.e. an antioxidant, a flavoring, and a preservative). Those of skill in the art will understand that a single ingredient can have more than one function. For example, one element of a formulation can be both an antioxidant and a preservative or flavoring, or serve some other desired function in a formulation. Preferred antioxidants include butylated hydroxytoluene (BHT), butylated hydroxyanisole (BHA), and combinations thereof. Suitable preservatives comprise methylparaben, methylparaben sodium, propylparaben, and combinations thereof. Propylparaben and methylparaben are preferred preservatives, and combinations of the two are more preferred.

Flavorings suitable to include in statin liquid solutions are fruit syrups such as grape syrup, grape cherry syrup, orange syrup, and cherry syrup, bubble gum, almond oil, anise oil, clove oil, lemon oil, licorice fluid extract, orange oil, peppermint oil, other mint oils, vanilla tincture, and various combinations thereof. Preferred flavorings include grape syrup, cherry syrup, and bubble gum. Those of skill in the art will recognize that one, two, three, or even more flavorings can be combined in a formulation to yield a desired flavor.

Other elements that optionally can be included in statin liquid formulations include amino acids, vitamins, minerals, phospholipids, cyclodextrins, triglycerides, diglycerides, monoglycerides, ionic surfactants, non-ionic surfactants, bile salts, fatty acids, sweeteners, buffers, or any combinations thereof. Those of skill in the art will recognize that the inclusion of such additional elements in any particular formulation is dependent, at least in part, upon the individuals to whom the formulation is to be administered. Similarly, those of skill in the art will recognize that the specific disease(s) being treated or objective(s) of treatment can effect the addition of elements to formulations.

As used herein, a "therapeutically effective amount" or "effective amount" of a statin drug or formulation described herein is the minimum amount necessary to, for example, increase or improve one or more muscle function parameters, such as, for example, contractility, fatigue, and/or muscle damage. Of course, one of skill in the art will recognize that the therapeutic level can vary depending on the individual being treated and the severity of the condition. For example, the age, body weight, and medical history of the individual patient can affect the therapeutic efficacy of a given dosage of a statin drug. A competent physician can consider these factors and adjust the dosing regimen to ensure the dose is achieving the desired therapeutic outcome without undue experimentation. It is also noted that the clinician and/or treating physician will know how and when to interrupt, adjust, and/or terminate therapy in conjunction with individual patient response. Accordingly, the "therapeutically effective amount" to be administered to a subject is governed by such considerations, and, as used herein, refers to the minimum amount necessary to prevent, ameliorate, treat, or stabilize, a neuromuscular disorder or condition as described herein. In some embodiments, the effective amount is sufficient to improve muscle function e.g., as measured in the Examples described herein or as measured according to a clinically accepted scale for MD severity, by at least about 5%, e.g., by at least about 10%, at least about 20%, at least about 30%, at least about 40%, at least about 50%, at least about 60%, at least about 70%, at least about 80%, at least about 90%, at least about 95%, at least about 96%, about 98%, about 99%, or 100%, as compared to muscle function in the absence of the statin drug.

In some embodiments, the effective amount is sufficient to reduce neuromuscular pathologies that occur in muscle cells or muscle tissue. Various established in vitro and in vivo assays can be used to determine an effective amount of the statin drug or derivative or stereoisomer thereof for inhibiting neuromuscular pathology in muscle cells, as described, for example, in the Examples. Exemplary measurable responses are muscle contractility and/or muscle fatigue, including meaurements of diaphragm function. Other measureable responses can be assessed by any of the following assays on a myogenic cell or muscle cell from a patient:

reduced calcium uptake by muscle cells, decreased collagen synthesis, altered morphology, altered lipid biosynthesis, decreased oxidative stress, and/or improved muscle fiber function, integrity, and/or survival. These parameters can be assessed, for example, using immunofluorescence and/or histochemical analyses of cross sections of muscle biopsies.

The improvement of muscle fiber function, integrity and/or survival can be assessed using at least one of the following assays: a detectable decrease of creatine kinase in blood, a detectable decrease of necrosis of muscle fibers in a biopsy cross-section of a muscle suspected to be dystrophic, and/or a detectable increase of the homogeneity of the diameter of muscle fibers in a biopsy cross-section of a muscle suspected to be dystrophic. Each of these assays is known to the skilled person. Creatine kinase can be detected in blood as described in Hodgetts et al (Hodgetts S., et al, (2006), Neuromuscular Disorders, 16: 591-602.2006). A detectable decrease of necrosis of muscle fibers can be assessed in a muscle biopsy, as described in Hodgetts et al (Hodgetts S., et al, (2006), Neuromuscular Disorders, 16: 591-602.2006) using biopsy cross-sections. A detectable increase of the homogeneity of the diameter of a muscle fiber can be assessed in a muscle biopsy cross-section as described in Hodgetts et al (Hodgetts S., et al, (2006), Neuromuscular Disorders, 16: 591-602.2006).

In some embodiments, an alleviation of one or more symptoms can be assessed by any of the following assays on the patient self: prolongation of time to loss of walking, improvement of muscle strength, improvement of the ability to lift weight, improvement of the time taken to rise from the floor, improvement in the nine-meter walking time, improvement in the time taken for four-stairs climbing, improvement of the leg function grade, improvement of the pulmonary function, improvement of cardiac function, improvement in the 6-minute walk test, improvement of the quality of life. Each of these assays is known to the skilled person. As an example, the publication of Manzur at al (Manzur A Y et al, (2008), Glucocorticoid corticosteroids for Duchenne muscular dystrophy (review), Wiley publishers, The Cochrane collaboration, the contents of which are herein incorporated by reference in their entireties) gives an extensive explanation of each of these assays. For each of these assays, as soon as a detectable improvement or prolongation of a parameter measured in an assay has been found, it will preferably mean that one or more symptoms of Duchenne Muscular Dystrophy or Becker Muscular Dystrophy has been alleviated in an individual using any of the methods described herein.

Accordingly, in some embodiments, the effective amount of the statin drug is sufficient to increase muscle contraction and/or decrease muscle fatigue by at least about 5%, e.g., by at least about 10%, at least about 20%, at least about 30%, at least about 40%, at least about 50%, at least a bout 60%, at least about 70%, at least about 80%, at least about 90%, at least about 95%, at least about 96%, about 98%, about 99%, or 100% or more, as compared to the absence of the statin drug.

By "reduce" or "inhibit" in terms of the neurodegenerative disorder treatment methods described herein is meant the ability to cause an overall decrease preferably of 20% or greater, 30% or greater, 40% or greater, 45% or greater, more preferably of 50% or greater, of 55% or greater, of 60% or greater, of 65% or greater, of 70% or greater, and most preferably of 75% or greater, 80% or greater, 85% or greater, 90% or greater, or 95% or greater, for a given parameter or symptom of a neurodegenerative disorder.

In some embodiments, the total daily dosage of a statin formulation administered in the methods described herein can range from about 0.1 mg to about 200 mg.

For example, the total daily dosage of simvastatin in formulations for use in the methods described herein ranges from about 1 mg to about 200 mg, about 20 mg to about 160 mg, about 20 mg to about 80 mg, about 30 mg to about 80 mg, about 40 mg to about 80 mg, about 40 mg to about 70 mg, about 40 mg to about 60 mg, or any whole number or fractional amount in between. A single dose can be formulated to contain about 1, 5, 10, 15, 20, 25, 30, 35, 40, 45, 50, 55, 60, 65, 70, 75, 80, 85, 90, 95, 100, 120, 140, 160, 180, or 200 mg of simvastatin. In some embodiments, a single dose contains about 30, 35, 40, 45, 50, 55, 60, 65, 70, 75, 80, 85, or 90 mg of simvastatin.

For example, the total daily dosage of atorvastatin in formulations for use in the methods described herein ranges from about 1 mg to about 200 mg, about 20 mg to about 160 mg, about 20 mg to about 80 mg, about 30 mg to about 80 mg, about 30 mg to about 70 mg, about 30 mg to about 50 mg, or any whole number or fractional amount in between. A single dose can be formulated to contain about 1, 5, 10, 15, 20, 25, 30, 35, 40, 45, 50, 55, 60, 65, 70, 75, 80, 85, 90, 95, 100, 120, 140, 160, 180, or 200 mg of atorvastatin. In some embodiments, a single dose contains about 30, 35, 40, 45, or 50, mg of atorvastatin.

For example, the total daily dosage of cerivastatin in formulations for use in the methods described herein ranges from about 0.1 mg to about 100 mg, about 0.1 mg to about 20 mg, about 0.1 mg to about 10 mg, about 0.1 mg to about 5 mg, about 0.2 mg to about 5 mg, about 0.2 mg to about 2 mg, about 0.2 mg to about 1 mg, about 0.2 mg to about 0.5 mg, or any whole number or fractional amount in between. A single dose can be formulated to contain about 0.1, 0.2, 0.3, 0.4, 0.5, 0.6, 0.7, 0.8, 0.9, 1, 5, or 10 mg of cerivastatin. In some embodiments, a single dose contains about 0.1, 0.2, 0.3, 0.4, 0.5, 0.6, 0.7, 0.8, 0.9, or 1 mg of cerivastatin.

For example, the total daily dosage of fluvastatin in formulations for use in the methods described herein ranges from about 1 mg to about 200 mg, about 10 mg to about 100 mg, about 10 mg to about 60 mg, about 10 mg to about 50 mg, about 20 mg to about 50 mg, or about 20 mg to about 40 mg, or any whole number or fractional amount in between. A single dose can be formulated to contain about 1, 5, 10, 15, 20, 25, 30, 35, 40, 45, 50, 55, 60, 65, 70, 75, 80, 85, 90, 95, 100, 120, 140, 160, 180, or 200 mg of fluvastatin. In some embodiments, a single dose contains about 1, 5, 10, 15, 20, 25, 30, 35, 40, 45, 50, 55, or 60 mg of fluvastatin.

For example, the total daily dosage of lovastatin in formulations for use in the methods described herein ranges from about 1 mg to about 200 mg, about 20 mg to about 160 mg, about 20 mg to about 80 mg, about 30 mg to about 80 mg, about 30 mg to about 70 mg, about 30 mg to about 50 mg, or any whole number or fractional amount in between. A single dose can be formulated to contain about 1, 5, 10, 15, 20, 25, 30, 35, 40, 45, 50, 55, 60, 65, 70, 75, 80, 85, 90, 95, 100, 120, 140, 160, 180, or 200 mg of lovastatin. In some embodiments, a single dose contains about 30, 35, 40, 45, or 50, mg of lovastatin.

For example, the total daily dosage of pitavastatin in formulations for use in the methods described herein ranges from about 0.1 mg to about 100 mg, about 0.5 mg to about 20 mg, about 0.5 mg to about 10 mg, about 1 mg to about 5 mg, about 1 mg to about 3 mg, or any whole number or fractional amount in between. A single dose can be formulated to contain about 0.5, 1, 1.5, 2, 2.5, 3, 3.5, 4, 4.5, 5, or 10 mg of pitavastatin. In some embodiments, a single dose contains about 1, 1.5, 2, 2.5, 3, 3.5, or 4 mg of pitavastatin.

For example, the total daily dosage of pravastatin in formulations for use in the methods described herein ranges from about 1 mg to about 200 mg, about 20 mg to about 160 mg, about 20 mg to about 80 mg, about 30 mg to about 80 mg, about 30 mg to about 70 mg, about 30 mg to about 50 mg, or any whole number or fractional amount in between. A single dose can be formulated to contain about 1, 5, 10, 15, 20, 25, 30, 35, 40, 45, 50, 55, 60, 65, 70, 75, 80, 85, 90, 95, 100, 120, 140, 160, 180, or 200 mg of pravastatin. In some embodiments, a single dose contains about 30, 35, 40, 45, or 50, mg of pravastatin.

For example, in general, the total daily dosage of rosuvastatin in formulations of the present invention ranges from about 1 mg to about 200 mg, about 1 to about 160 mg, about 1 to about 80 mg, about 5 to about 80 mg, about 10 to about 80 mg, or any whole number or fractional amount in between. A single dose can be formulated to contain about 1, 5, 10, 15, 20, 25, 30, 35, 40, 60, 80, 100, 120, 140, 160, 180, or 200 mg of rosuvastatin. In some embodiments, a single dose contains about 10, 15, 20, 30, 40, 60, or 80 mg of rosuvastatin.

For children and adolescents, dosing is usually more conservative compared to adults so that the potential for dose-related adverse events is reduced. In adolescents (about 10-17 years old), the usual starting dose of a statin drug, e.g., simvastatin, is 10 mg/day in the evening. The maximum preferred dosage for an adolescent is 40 mg/day with doses ranging from 10-80 mg/day. For children less than 10 years of age, the usual starting dose is 5 mg/day in the evening, and the recommended dosage range is 5-20 mg/day in the evening. In general, adjustments should be made at intervals of about 4 weeks or longer, but doses can be individualized and adjusted at any time as needed to achieve the desired therapeutic goal.

It is expected that for most children and adolescents, the preferred or recommended dosages will be used; however, doses can be adjusted to meet individual needs. Thus, a child or adolescent can receive the equivalent of 0.5-120 mg/day of a statin, e.g. simvastatin, using, for example, an oral formulation, and preferably the adolescent receives the equivalent of 5-40 mg/day of statin using the oral formulation and the child receives the equivalent of 5-20 mg/day of statin using the oral formulation. The liquid formulation can be given as a single dose, or in multiple doses. It can be given daily, preferred, or at multiple day intervals. An advantage of using the liquid formulation is the dosage can be more precisely calculated and provided. For example, a child or adolescent may receive the equivalent of 0.5, 1, 1.5, 2, 2.5, 3, 3.5, 4, 4.5, 5, 5.5, 6, 6.5, 7, 7.5, 8, 8.5, 9, 9.5, 10, 10.5, . . . 16, 16.5, 17, 17.5, 18, 18.5, 19, 19.5, 20, 20.5, . . . 36, 36.5, 37, 37.5 38, 38.5, 39, 39.5, 40, 40.5, . . . 78, 78.5, 79, 79.5, 80, 80.5 . . . 118, 118.5, 119, 119.5, or even 120 mg/day of statin using the liquid formulation. Single doses can include 0.5 to 25 mg/ml of statin, preferred doses include 2-5 mg/ml statin.

In some embodiments of the methods described herein, the statin drug is administered in an open acid dose form. In some embodiments of the methods described herein, the statin drug is administered in a lactone pro-drug form.

Neuromuscular Disorders

The present disclosure is directed to methods of treating neuromuscular diseases using statins. In certain further embodiments of the methods described herein, the neuromuscular diseases include Duchenne muscular dystrophy, Becker muscular dystrophy, Limb-girdle muscular dystrophies, Ullrich congenital muscular dystrophy, inflammatory myositis, muscle atrophy, and Amyotrophic lateral sclerosis.

As demonstrated herein, statin drugs are unexpectedly therapeutic when used in methods of treatment of neuromuscular disorders, such as muscular dystrophies. Accordingly, provided herein are methods of treating a subject having or at risk for a neuromuscular disorder comprising administering a therapeutically effective amount of a statin drug.

Neuromuscular disorders or diseases refer to those disorders in which muscle function is impaired, either directly due to pathologies of the muscle (myopathic disorders), and/or indirectly, due to pathologies of nerves or neuromuscular junctions (neuropathic disorders), and include muscular dystrophies, inflammatory myopathies, and muscle atrophies. Accordingly, as used herein the term "neuromuscular disorders" encompasses muscular dystrophies (including but not limited to severe or benign X-linked muscular dystrophy, limb-girdle dystrophy, facioscapulohumeral dystrophy, myotonic dystrophy, distal muscular dystrophy, progressive dystrophic ophthalmoplegia, oculopharyngeal dystrophy, Duchenne's muscular dystrophy, and Fukuyama-type congenital muscular dystophy); polymyositis; amyotrophic lateral sclerosis (ALS); muscle atrophy; muscle atrophy due to carpal tunnel syndrome; muscle wasting associated with congestive obstructive pulmonary disease; congenital myopathy; myotonia congenital; familial periodic paralysis; paroxysmal myoglobinuria; myasthenia gravis; Eaton-Lambert syndrome; secondary myasthenia; denervation atrophy; paroxymal muscle atrophy; muscle atrophy associated with cerebrovascular accidents (stroke), Parkinson's disease, multiple sclerosis, Huntington's (Huntington's chorea) and Creutzfeldt-Jakob disease; and sarcopenia, cachexia and other muscle wasting syndromes.

The term "degenerative muscle condition" refers to conditions, disorders, diseases and injuries characterized by one or more of muscle loss, muscle degeneration or wasting, muscle weakness, and defects or deficiencies in proteins associated with normal muscle function, growth or maintenance. In some embodiments, a degenerative muscle condition is sarcopenia or cachexia. In some embodiments, a degenerative muscle condition is one or more of muscular dystrophy, muscle atrophy, muscle wasting or muscle degeneration.

"Muscular dystrophy" refers to a group of more than 30 hereditary muscle diseases characterized by progressive skeletal muscle weakness, degeneration of skeletal muscle fibers, defects in certain muscle proteins, and death of muscle cells and tissue, which are distinguished clinically by the selective distribution of skeletal muscle weakness. Muscular dystrophies are caused by progressive degeneration of skeletal muscle fibers. Lack of one of several proteins located either at the plasma membrane or within internal membranes, increases the probability of damage during contraction, and eventually leads to fiber degeneration, accompanied by severe local inflammation with infiltration of immune-competent cells. As muscular dystrophy progresses and muscles weaken, fixations (contractures) can develop in joints, in which muscles and tendons shorten, restricting the flexibility and mobility of joints and muscles. Muscular dystrophies are multi-system disorders with manifestations in numerous body systems including the heart, gastrointestinal and nervous systems, endocrine glands, skin, eyes, and other organs. Muscular dystrophies are associated with various clinical symptoms, including muscle damage, muscle wasting, muscle weakness, muscle degeneration, muscle atrophy, weight loss, and elevated serum creatine kinase levels.

The two most common forms of muscle dystrophy are Duchenne and Becker dystrophies, each resulting from the inheritance of a mutation in the dystrophin gene, which is located at the Xp21 locus. Other muscular dystrophies include, but are not limited to, limb-girdle muscular dystrophies, fascioscapulohumeral (Landouzy-Dejerine) muscular dystrophy, congenital muscular dystrophy, myotonic dystrophy, and Emery-Dreifuss muscular dystrophy. Accordingly, as used herein, the term "muscular dystrophy" includes Duchenne Muscular Dystrophy; Becker Muscular Dystrophy; Emery-Dreifuss Muscular Dystrophy; Limb-Girdle Muscular Dystrophies; Facioscapulohumeral Muscular Dystrophy (also known as Landouzy-Dejerine); Myotonic Dystrophy; Oculopharyngeal Muscular Dystrophy; Distal Muscular Dystrophy; and Congenital Muscular Dystrophies.

Duchenne muscular dystrophy and Becker muscular dystrophy are similar in that these dystrophies share similar patterns of muscle weakness and disability and are inherited in the same way. Typically, subjects in need of treatment for Duchenne or Becker muscular dystrophies have trouble walking and eventually become wheelchair dependent. Generally, an arbitrary means of distinguishing between Duchenne muscular dystrophy and Becker muscular dystrophy depends on whether the affected subject can still walk at 16 years of age. Subjects with Duchenne muscular dystrophy are generally wheelchair bound by their teenage years. More specifically, a muscle biopsy of a subject affected with Duchenne muscular dystrophy will show more disabling change as compared to a subject affected with Becker muscular dystrophy. In addition, Becker muscular dystrophy biopsies typically show a much lower amount of dystrophin or a smaller dystrophin produced by an in frame deletion, producing a partially functional dystrophin.

Duchenne muscular dystrophy and the milder allelic disorder, Becker muscular dystrophy (BMD), are caused by mutations in the dystrophin gene, which encodes an actin binding protein that links the actin cytoskeleton with the extracellular matrix, forming the dystrophin-associated glycoprotein complex (DGC) (Durbeej and Campbell, 2002; Ehmsen et al., 2002; Rando, 2001). The dystrophin deficiency leads to loss of other DGC members, including nNOSμ (Ibraghimov-Beskrovnaya et al., 1992; Waite et al., 2009). The dystrophin gene encodes a large 427 kDa protein that functions in linking the extracellular matrix to the muscle fiber cytoskeleton. The amino terminus on dystrophin binds to filamentous actin in contact with the contractile apparatus of skeletal muscle, while a cysteine-rich domain near the carboxyl terminus binds to dystroglycan proteins localized to the fiber membrane in connection with other membrane proteins that constitute the dystrophin glycoprotein complex (DGC). The absence of dystrophin expression causes a concomitant decrease in DGC members. Without wishing to be bound or limited by theory, it is believed that loss of dystropin and the resulting DGC complex compromises the integrity of skeletal muscle membranes, which undergo damage after repeated cycles of contractile activity. Membrane damage is further thought to cause creatine kinase release, stimulate the influx of calcium, and induce the recruitment of immune T cells, macrophages, and mast cells, culminating in muscle fiber necrosis. The regenerative capacity of these cells becomes exhausted in Duchenne muscular dystrophy patients, thus giving way to accumulated fibrosis and fatty deposits that exacerbates the muscle wasting process.

Limb Girdle muscular dystrophies include at least ten different inherited disorders that can further be classified into two categories, autosomal-dominant (LGMD 1) and autosomal-recessive (LGMD 2) syndromes. The symptoms of most Limb Girdle muscular dystrophies typically begin with pelvic muscle weakness starting in childhood to young adulthood. Later, there is an onset of shoulder weakness with progression to significant loss of mobility or wheelchair dependence over the next 20-30 years.

The defective gene causing most autosomal-dominant type Limb Girdle muscular dystrophies has not yet been discovered, but the diseases have been linked to mutations in various chromosomes. For example, LGMD 1A type dystrophy has been linked to chromosome 5. Additionally, LGMD 1B type dystrophy has been linked to chromosome 1. Other chromosomes that have been linked to the autosomal-dominant type Limb Girdle muscular dystrophies include chromosomes 3 and 7. Several of the autosomal-recessive type Limb Girdle muscular dystrophies are due to mutations in the dystrophin-associated glycoproteins.

The methods described herein can, in some embodiments, be used to treat an inflammatory myopathy. Inflammatory myopathies refer to diseases or abnormal conditions of the striated skeletal muscles. The cause of most inflammatory myopathies is unknown. Typically, inflammatory myopathies are believed to result from an autoimmune reaction, whereby the body's own immune system attacks the muscle cells. Examples of inflammatory myopathies include polymyositis and dermatomyositis. Symptoms of polymyositis include muscle inflammation and muscle tenderness. The onset of symptoms may be acute, but the condition usually progresses slowly and, if left untreated, may compromise the subject's ability to walk. Subjects in need of treatment for dermatomyositis have similar symptoms as with polymyositis, but additionally show signs of a distinctive skin rash. Specifically, a violet-colored or dusky red rash breaks out over the subject's face, eyelids, and areas around their nails, knuckles, elbows, knees, chest, and back. Dermatomyositis typically occurs in adult subjects in their late 40s to early 60s or in children between the ages of 5 and 15.

The methods described herein can also be used to treat muscle atrophy, in some embodiments. Muscle atrophy can be the result of a disorder or condition such as, cancer cachexia, AIDS cachexia, or cardiac cachexia. Cachexia is generally associated with the massive loss (up to 30% of total body weight) of both adipose tissue and skeletal muscle mass that may occur as a side effect of many diseases such as cancer, AIDS, and chronic heart failure. The loss of adipose tissue and skeletal muscle mass can lead to anorexia, early satiety, fatigue, generalized muscle weakness, decreased muscle function, and progressive muscle wasting. Muscle atrophy can also be induced by the loss of innervation or damage to innervation of the muscle tissue. Specifically, diseases such as chronic neuropathy and motor neuron disease can cause damage to innervation. Moreover, many times a physical injury to the nerve can lead to damage to the innervation of the muscle tissue.

Alternatively, muscle atrophy can be the result of environmental conditions such as during spaceflight or as a result of aging or extended bed rest. Under these environmental conditions, the muscles do not bear the usual weight load, resulting in muscle atrophy from disuse.

The methods described herein can also be used, in some embodiments to treat other muscle diseases characterized by inflammation, oxidative stress, ischemia and/or fibrosis.

Subjects and Selection of Subjects

In some embodiments of the methods described herein, the subject to be treated with a statin drug is first selected. The determination as to whether a subject has a neuromuscular disorder, such as a muscular dystrophy, as well as the determination of a particular type of muscular dystrophy, can be made by any measure accepted and utilized by those skilled in the art. For example, diagnosis of subjects with muscular dystrophy is generally contingent on a targeted medical history and examination, biochemical assessment, muscle biopsy, or genetic testing.

In some embodiments, statin administration for treatment of a neuromuscular disease is commenced before the subject is 10 years of age.

In some embodiments, a subject's medical history can be used to diagnose or select a subject having a muscular dystrophy. Subjects with Duchenne muscular dystrophy, for example, are symptomatic before the age of 5 years, and experience difficulty running, jumping, and climbing steps. Proximal weakness causes individuals to use their arms in rising from the floor (i.e., Gowers' sign). Independent ambulation is often lost by 10-14 years of age, with subsequent deterioration in respiratory function and development of contractures and scoliosis. (See, e.g., Darras (2006) Continuum. 12: 33-75). Static cognitive impairment is common (Wicksell et al. (2004) Dev Med Child Neurol. 46:154-159). Approximately one third of boys with Duchenne muscular dystrophy develop cardiomyopathy by 14 years of age, and virtually all do after 18 years. Congestive heart failure and arrhythmias are common in end-stage Duchenne muscular dystrophy. (See, e.g., Kirchmann et al. (2005) Pediatr Cardiol. 26:66-72). Historically, most young men with Duchenne muscular dystrophy die in their late teens or early twenties from respiratory insufficiency or cardiac failure. Due to better respiratory care, specifically night time respiratory assistance, the average lifetime of DMD boys was recently determined to be 29 years. As a result of longer life time, more succumb to cardiac failure.

In some embodiments, biochemical assessments can be run to determine the levels of various constituents of muscle and muscle fibers. For example, measurement of blood plasma or serum creatine kinase levels can be used to diagnose or select a subject having muscular dystrophy. Specifically, when the total CK level is substantially elevated, it usually indicates injury or stress to one or more of the heart, brain, and skeletal muscle. Before the age of 5 years, serum creatine kinase levels are 10 to 200 times higher in subjects with Duchenne muscular dystrophy and Becker muscular dystrophy compared to normal levels. (See, e.g., Cardamone et al. (2008) Semin Neurol. 28:250-9). (Normal levels of CK vary with age and gender, as follows: Males, age 6-11 years: 150-499 u/l, 12-17 years: 94-499 u/l, >18 years: 52-336 u/l, Females, ages 6-7: 134-391 u/l, ages 8-14: 91-391 u/l, 15-17: 52-269 u/l, >18: 38-176 u/l.) In this context, then increased CK levels are at least 50% higher than the upper range of normal, and can be, e.g., at least 50%, at least 100%, at least 200% or more than this upper range, and indeed, as noted, CK levels in DMD can reach 10 to 200-fold higher than the upper range of normal. In some embodiments, a subject in need of treatment generates less electrical activity during muscle contraction as compared to a healthy subject and this can be detected by electromyography. In other embodiments, subjects affected by either Duchenne muscular dystrophy or Becker muscular dystrophy, can be diagnosed by measuring the level of dystrophin. Typically, in subjects with either Duchenne muscular dystrophy or Becker muscular dystrophy, the level of dystrophin is deficient; but, in a subject with Duchenne muscular dystrophy, the level is more severely deficient. Specifically, many Duchenne muscular dystrophy patients are null for dystrophin expression resulting from an out of frame deletion.

In some embodiments, muscle biopsy can be used to diagnose or select a subject as having muscular dystrophy. For example, muscle biopsy from Duchenne muscular dystrophy patients shows degeneration, regeneration, and variability of fiber size with replacement of muscle by fat and connective tissue. Muscle immunohistochemical studies with anti-dystrophin antibodies shows complete absence of staining in muscle from subjects with Duchenne muscular dystrophy and reduced staining in muscle from subjects with Becker muscular dystrophy. (Cardamone et al. (2008) Semin Neurol. 28:250-9).

In some embodiments, genetic testing can also be employed to diagnose or select a subject as having muscular dystrophy or a neuromuscular disorder. Techniques used in genetic testing include the polymerase chain reaction (PCR), Southern blotting, mutation scanning, and/or sequence analysis. (See, e.g., Darras (2006) Continuum. 12: 33-75). DNA extracted from blood or white cells can be used for such diagnoses. Deletions in the dystrophin gene are detected in 65% of patients with Duchenne muscular dystrophy and 85% of patients with Becker muscular dystrophy. Quantitative assays of dystrophin can be used to predict phenotype. Patients with Duchenne muscular dystrophy, for example, have less than 5% of the normal quantity of dystrophin Patients with Becker muscular dystrophy have at least 20% normal dystrophin levels. (See Cardamone et al. (2008) Semin Neurol. 28:250-9).

In some embodiments, magnetic resonance imagining (MRI) can also be employed to diagnose or select a subject as having muscular dystrophy or a neuromuscular disorder. During an MRI, cross-sectional images of muscle are generated by a magnetic field and radio waves. The image generated by an MRI can reveal abnormalities in the muscle, such as inflammation, damage, or infection.

The term "muscle function" refers to the ability of muscle to perform a physiologic function, such as contraction as measured by the amount of force generated during either twitch or tetanus. Other methods for assessing muscle function are well known in the art and include, but are not limited to, measurements of muscle mass, grip strength, serum creatine kinase (CK) level(s), activities of daily living, motion or strength tests, tissue histology (e.g., H&E staining, or collagen III staining), or tissue imaging. Nonlimiting illustrative methods for assessing muscle function are also set forth in the Examples.

In some embodiments of the methods described herein, the subject having or at risk for a neuromuscular disease does not have/has not been previously diagnosed with high cholesterol levels or does not have/has not been previously diagnosed with a cardiovascular disease.

Typically, statins are administered in order to lower cholesterol levels and therefore reduce the risk or for treatment of cardiovascular diseases. In contrast, the methods described herein are directed to subjects having or at risk for a neuromuscular disorder, where any deficiency or ailment in the function or activity of the heart is not caused by high cholesterol levels or vascular issues (i.e., atherosclerosis), but due to deficiencies or issues with cardiac muscle function, not involving the cardiac vasculature. There are two major classes of circulating cholesterol, termed "high density lipoproteins" (HDL) and "low density lipoproteins" (LDL). HDL is commonly referred to as "good cholesterol" as it operates to remove excess cholesterol from the arteries and transport it to the liver. LDL is commonly referred to as "bad cholesterol", as it delivers cholesterol to the tissues, thus contributing to cholesterol accumulation in arterial macrophages, a first step in the development of atherosclerotic plaques. Patients with cholesterol levels higher than normal, in particular LDL cholesterol, a condition commonly referred to as hypercholesterolemia, are at high risk of developing atherosclerosis.

As used herein, a subject having "high cholesterol levels" or "poor cholesterol levels" is one in which the total cholesterol level is at least 200 mg/dL, typically at least 240 mg/dL. A subject can be considered to have "high cholesterol levels" if their LDL cholesterol levels are greater than 100 mg/dL, greater than 130 mg/dL, greater than 160 mg/dL, or greater than 190 mg/dL. A subject can be considered to have poor cholesterol levels if their HDL cholesterol levels are less than 60 mg/dL, typically less than 40 mg/dL.

As used herein, a subject having a "cardiovascular disease" has any condition in which statins are typically used to reduce blood cholesterol levels including atherosclerosis, coronary heart disease (CHD), cerebrovascular disease, and peripheral vascular disease. Cardiovascular disorders are acute manifestations of CVD and include myocardial infarction, stroke, angina pectoris, transient ischemic attacks, and congestive heart failure. Cardiovascular disease, including atherosclerosis, usually results from the build-up of cholesterol, inflammatory cells, extracellular matrix and plaque. To be clear, a cardiovascular disease as used herein does not include any disease or disorder caused by deficiencies or issues with cardiac muscle function that are not secondary to problems with the cardiac vasculature.

In some embodiments of the methods described herein, the subject having or at risk for a neuromuscular disease does not have/has not been previously diagnosed with familial hypercholesterolemia. As used herein, "familial hypercholesterolemia" (FH) refers to an autosomal dominant disorder that causes severe elevations in total cholesterol and low-density lipoprotein cholesterol (LDLc). The most common genetic defects in FH are LDLR mutations (prevalence 1 in 500, depending on the population), ApoB mutations (prevalence 1 in 1000), PCSK9 mutations (less than 1 in 2500) and LDLRAP1. Heterozygous FH is normally treated with statins, bile acid sequestrants, or other lipid lowering agents that lower cholesterol levels. Homozygous FH often does not respond to medical therapy and can require additional treatments, including LDL apheresis (removal of LDL in a method similar to dialysis) and occasionally liver transplantation.

The methods and formulations described herein can, in some embodiments, be used in combination with other drugs or treatments that are of therapeutic benefit in treating or managing a neuromuscular disorder. Such drugs or treatments include, but are not limited to, gene therapy treatments, such as gene therapy targeting the dystrophin gene, such as those described in International Publication No. WO 2015/035364, the contents of which are herein incorporated by reference in their entirety, and antisense compound treatments to induce exon skipping in mutated forms of the human dystrophin gene; corticosteroids; phenytoin, procainamide, or quinine administration; dietary supplements, such as creatine and glutamine; and antioxidant treatments, such as N-acetylcysteine (as described in J. Physiol. 586.7 (2008) pp 2003-2014, the contents of which are herein incorporated by reference in their entirety).

In those embodiments where the combination treatment involves compositions and/or methods related to exon skipping, any such compositions and methods described in any of US Patent Publications 20150166996, 20150073037, 20150057330, 20150045413, 20140350069, 20140329881, 20140094500, and 20120029060, the contents of each of which are herein incorporated by reference in their entireties, can be used. As used herein, "exon skipping" refers to the induction in a cell of a mature mRNA that does not contain a particular exon that is normally present therein. Exon skipping is performed by providing a cell expressing the pre-mRNA of said mRNA with a molecule capable of interfering with essential sequences such as, for example, the splice donor or splice acceptor sequence required for splicing of said exon, or a molecule that is capable of interfering with an exon inclusion signal that is required for recognition of a stretch of nucleotides as an exon to be included in the mRNA. The term pre-mRNA refers to a non-processed or partly processed precursor mRNA that is synthesized from a DNA template in the cell nucleus by transcription.

EXAMPLES

Example 1: Statins are Therapeutic for Muscular Dystrophy in the Mdx Model of DMD As described herein, mdx mice were treated with Simvastatin, a commonly prescribed and extensively researched statin that lowers LDL cholesterol and improves cardiovascular system health (1, 6, 11, 23). While the benefits of statins on atherosclerosis-related outcomes are well established, it is less well known that these drugs also significantly improve skeletal muscle health in experimental and clinical limb ischemia (3, 8, 10, 17). This is important because DMD has been characterized as a functional ischemic disease, with impaired muscle perfusion associated with muscle contractions in both mdx mice and DMD boys (5, 26). Consistent with these observations, the data described herein show dramatic reductions in whole-body muscle damage and significant improvements in diaphragm and cardiac muscle function after long-term Simvastatin treatment of mdx mice. Therefore, the data provided herein demonstrate that statins represent a promising, novel, and completely unexpected therapeutic approach for DMD and other neuromuscular disorders. Importantly statin therapy has salutary effects in cardiac as well as skeletal muscle, both of which are impaired in DMD. From a clinical standpoint, statins are one of the most commonly prescribed drugs, prescribed to ~25 million people worldwide, and many large clinical trials have evaluated their efficacy and side effects. One side effect that is often discussed and researched is statin-induced myopathy, a general term to describe muscle pain or weakness with or without mildly raised CK levels in the blood. The overall incidence of statin-induced myopathy is relatively low (2-5% based on several clinical studies), and varies depending on a number of variables including: statin type, dose, patient's age, and predisposing genetic factors (14). Of particular relevance to DMD patients, a number of statins are FDA approved for treatment of familial hypercholesterolemia in children older than 10 years of age, and have been shown to be well tolerated (20). Furthermore, in animal studies of ischemic muscle diseases, statins improve skeletal muscle health, as shown by significant reductions in plasma CK activity, muscle necrosis and inflammation (17), and increased angiogenesis which promotes greater blood flow (18). However, statins are still widely perceived to be relatively toxic to muscle, a perception that has thus far precluded their use in muscular dystrophies. As described herein, statins preserve both skeletal and cardiac muscle health in dystrophic mice. Accordingly, statins represent a completely new class of therapeutic compounds for treatment of DMD and other human neuromuscular diseases.

An outline of the biochemical pathways blocked by these drugs (FIG. 1) illustrates how statins regulate nNOS and NOX2 in dystrophic muscle. Statins inhibit HMG CoA-reductase, the rate-limiting enzyme involved in the production of cellular cholesterol. In the liver, low intracellular cholesterol triggers a feedback pathway that causes greater uptake of circulating LDL cholesterol via the LDL receptor, resulting in lower blood LDL concentrations. However, inhibition of HMG CoA-reductase by statins also prevents the isoprenylation (geranylgeranylation) of small GTPase proteins such as racl and rhoA, which require this lipid anchor for membrane targeting and activation Inhibition of this pathway is believed to mediate the cholesterol-independent or so-called 'pleiotropic' effects of statins in the cardiovascular system (27).

Of particular relevance for DMD, NOX2 and racl are upregulated in mdx skeletal and cardiac muscle. Racl is essential for activation of NOX2, the major source of reactive oxygen species (ROS) and oxidative stress in mdx muscle (15, 29). NOX2 also triggers excessive Ca2+ influx via stretch-activated channels (SAC) in skeletal muscle (15, 29) and RyR2 in cardiac muscle (25) of dystrophic mice. Therefore, the data described herein indicate that by preventing racl activation, statins inhibit NOX2 activity and reduce muscle damage due to oxidative stress and raised intracellular Ca2+ concentrations (see FIG. 1). In contrast to NOX2, nNOS and its downstream signaling pathways are decreased in mdx and DMD muscles and this leads to functional ischemia, inflammation, and loss of muscle function, all of which can be improved with drugs such as Sildenafil and Tadalafil, which boost NO-cGMP signaling by inhibiting PDE5 (16, 24, 26). Interestingly, in addition to nNOS, a recent study also showed decreased eNOS activity in endothelial cells of mdx mice, which contributed to functional ischemia, impaired angiogenesis and muscle damage (21). RhoA decreases nNOS and eNOS expression and activity in the vasculature and other tissues and this is prevented by statins (9, 12, 13). Therefore, without being bound or limited by theory, we propose herein that statins increase NOS signaling in skeletal muscle and/or blood vessels, by inhibition of RhoA, which decreases functional ischemia and reduces muscle damage (see FIG. 1, for example).

Figure 3:
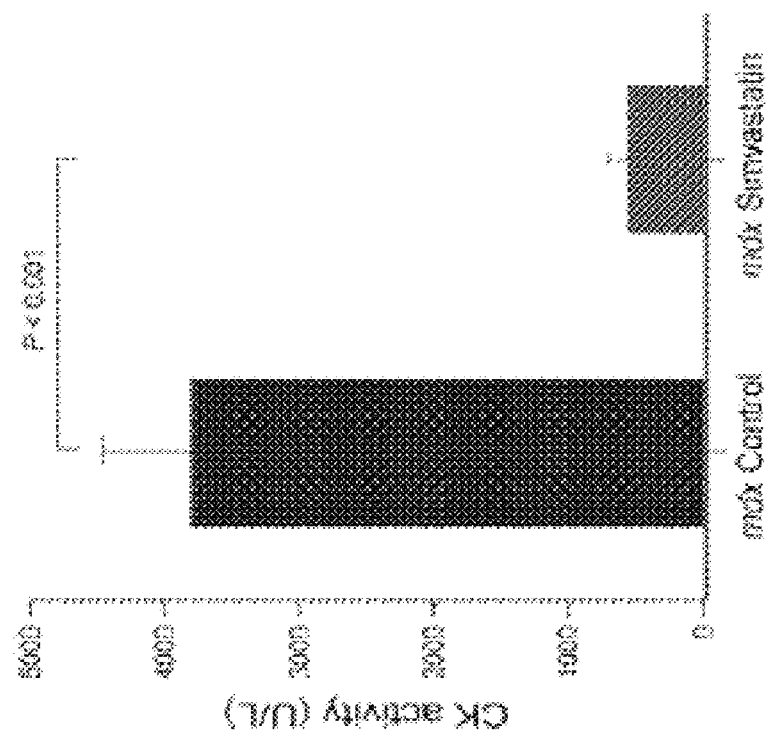
FIG. 3 shows that serum creatine kinase (CK) levels are dramatically reduced in mdx mice (n=10) by simvastatin treatment (n=9).

In studies described herein, we have demonstrated that long-term (8 months) treatment of mdx mice with Simvastatin in the drinking water (10 mg/kg/day) improved overall health and physiological function of skeletal muscle. The gold-standard clinical measurement to quantify whole-body muscle damage in DMD and other neuromuscular diseases is the CK activity level in the blood. Like DMD patients, mdx mice also have a substantially increased (10 fold or more) CK activity level compared to normal WT mice (values below 200 U/L). As shown in FIG. 3, Simvastatin treatment of mdx mice (n=9) dramatically reduced CK levels by ~8 fold compared to untreated mdx mice (n=10). This effect was highly statistically significant (P<0.001). Therefore, Simvastatin appears to substantially reduce whole-body muscle damage in mdx mice over a long-term treatment period. This is an important finding since the common dogma is that statins can induce muscle damage and CK release. Our studies indicate—to the contrary—that dystrophic muscles respond very differently to statins than normal muscles.

Figure 4:
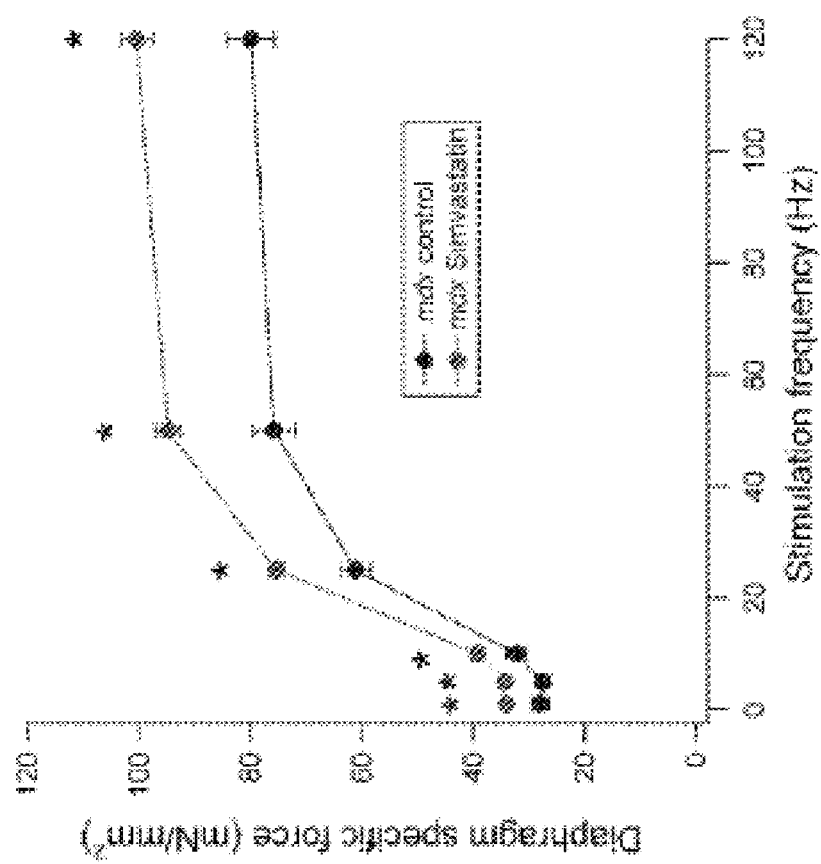
FIG. 4 shows that diaphragm specific force is significantly increased (*$P<0.01$) at all stimulation frequencies by Simvastatin (n=9) compared to Control mdx mice (n=9).

Next, we tested the effect of Simvastatin on diaphragm muscle function ex vivo. As shown in FIG. 4, Simvastatin significantly improved specific muscle force (force normalized to cross-sectional area) by 25%, over the full range of stimulation frequencies (1 to 120 Hz). As mentioned earlier, many mdx mouse studies do not include diaphragm function to evaluate the efficacy of a therapeutic compound. Therefore, it is often difficult to fully evaluate the therapeutic potential of these compounds. When compared with results obtained with a clinically relevant dystrophin gene therapy approach, the magnitude of increased diaphragm force in Simvastatin-treated mice (25%) is quite impressive. Specifically, systemic delivery of a micro-dystrophin-expressing AAV vector to mdx mice provides a slightly lower (20%) average improvement in diaphragm specific force.

Figure 5:
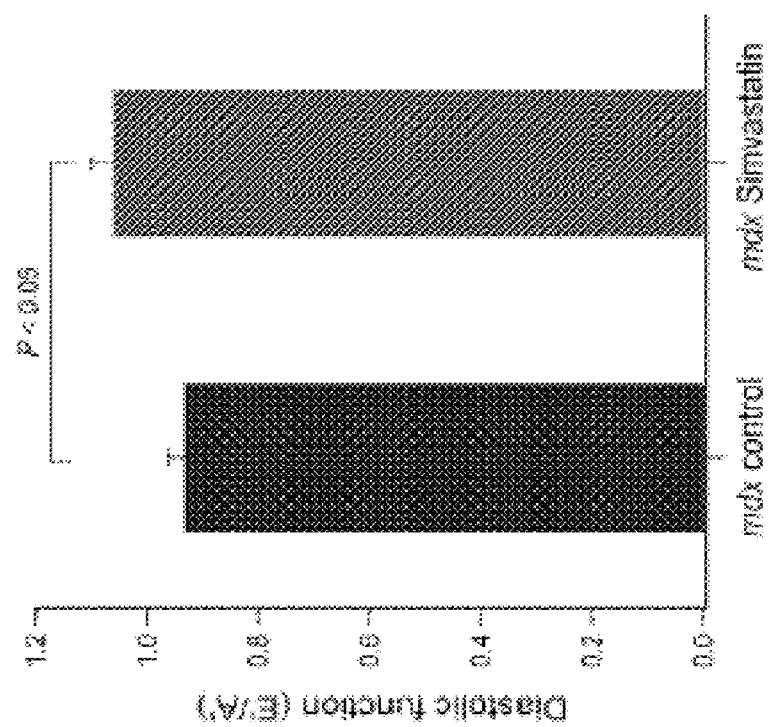
FIG. 5 shows that diastolic function, measured by the E"/A' ratio is below 1.0 in mdx Control mice (n=10) indicating early diastolic dysfunction, but is maintained above 1.0 in Simvastatin treated mdx mice (n=9). The value for normal wild type animals of the same age is approximately 1.2.
Figure 6:
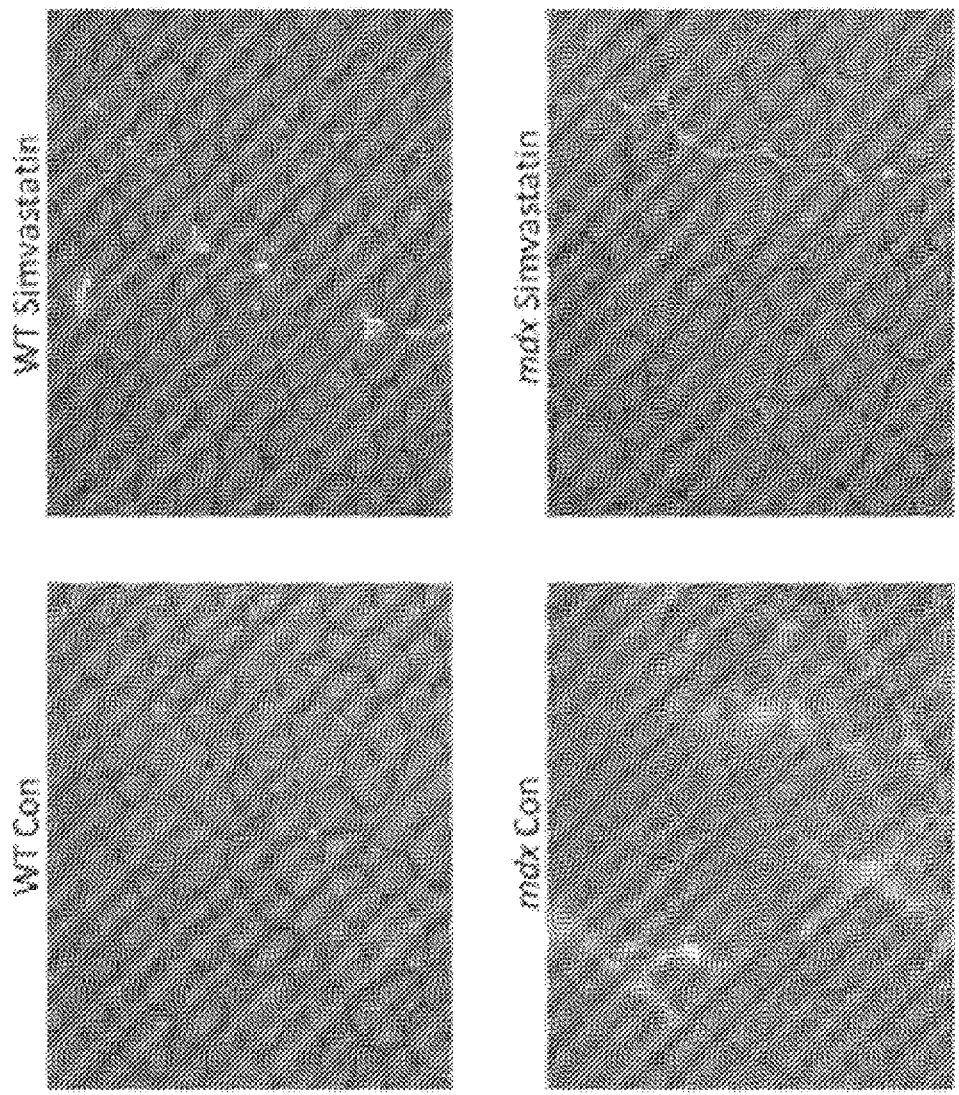
FIG. 6 shows H&E staining of TA muscles from WT and mdx mice with or without 8 months of Simvastatin treatment in the drinking water. H&E staining shows no evidence of muscle damage or inflammation in WT mice treated for 8 months with Simvastatin. The dose used (5-10 mg/kg/day) is equivalent to a low to moderate dose in humans. Muscles from both mdx Control mice and mdx mice receiving Simvastatin had large numbers of central nuclei, indicating muscle regeneration. However, there was significantly less inflammatory cell infiltration in the Simvastatin-treated mdx mice compared to untreated mdx mice ($P<0.05$).

We also evaluated cardiac function in mdx mice using echocardiography. Cardiomyopathy develops relatively slowly in mdx mice, however by 8 or 9 months of age early diastolic dysfunction is measurable, using Doppler tissue imaging (DTI). We used the E'/A' ratio, a measure of diastolic function, which should be >1 in a normal heart. However, in untreated mdx mice, this ratio dropped below 1, indicating early diastolic dysfunction. Importantly, Simvastatin treatment maintained this ratio above 1, indicating that Simvastatin prevents early left ventricular diastolic dysfunction in mdx mice (FIG. 5).

Taken together, the data provided herein demonstrate that statins, such as Simvastatin, improve overall muscle health in mdx mice, as highlighted by the dramatic reduction in plasma CK activity, and the enhanced physiological function of the diaphragm and cardiac muscle. Given that respiratory muscle weakness and cardiac dysfunction are the two major causes of death in DMD patients, a drug that can target both of these tissues has major therapeutic advantages for the treatment of DMD. From a clinical perspective, statins have no statistically significant side-effects, including myopathy, in children treated for familial hypercholesterolemia and are FDA-approved for use in children 10 years or older.

Figure 8A:
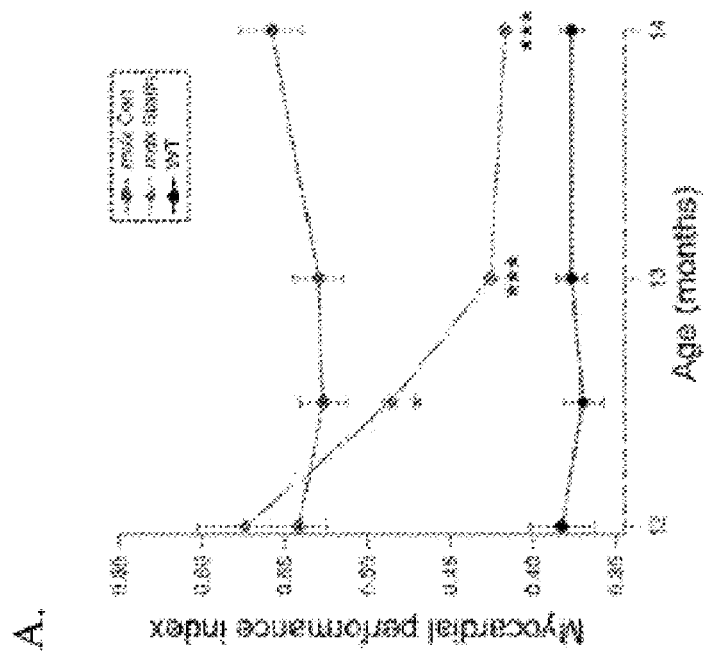
FIG. 8A shows myocardial performance index (MPI) as measured at 12 months and then over the next 2 months in WT and mdx Con mice or mdx mice receiving Simvastatin.
Figure 8B:
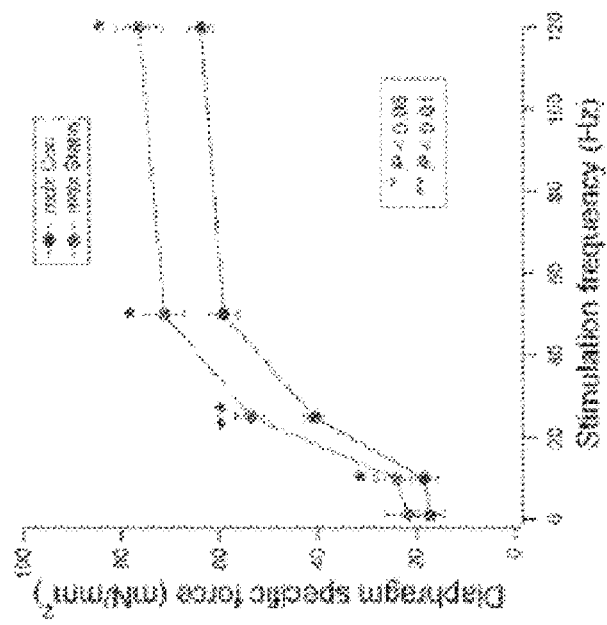
FIG. 8B shows diaphragm specific force measured in the same mdx mice as FIG. 8A.

The data contained herein also indicate that statin treatment reverses several aspects of the dystrophic phenotype associated with myopathies including muscular dystrophy. In FIG. 8A, a dramatic reversal of cardiac dysfunction is shown in 12-month-old mdx mice treated with Simvastatin over 2 months. The key parameter used to assess cardiac function was the Myocardial Performance Index (MPI), a global measure of left ventricular systolic and diastolic function. Importantly, a study on DMD patients, that did not have any overt signs or symptoms of cardiac dysfunction, found that MPI is significantly increased by as early as 10 years of age, before other more commonly used measures (FS and EF) become abnormal. Therefore, MPI is a more sensitive measure of early cardiac dysfunction in both DMD and mdx mice. Also, in FIG. 8B, the same mice showed a significant improvement in diaphragm specific force with Simvastatin treatment over a wide range of stimulation frequencies.

Figures 7A, 7B:
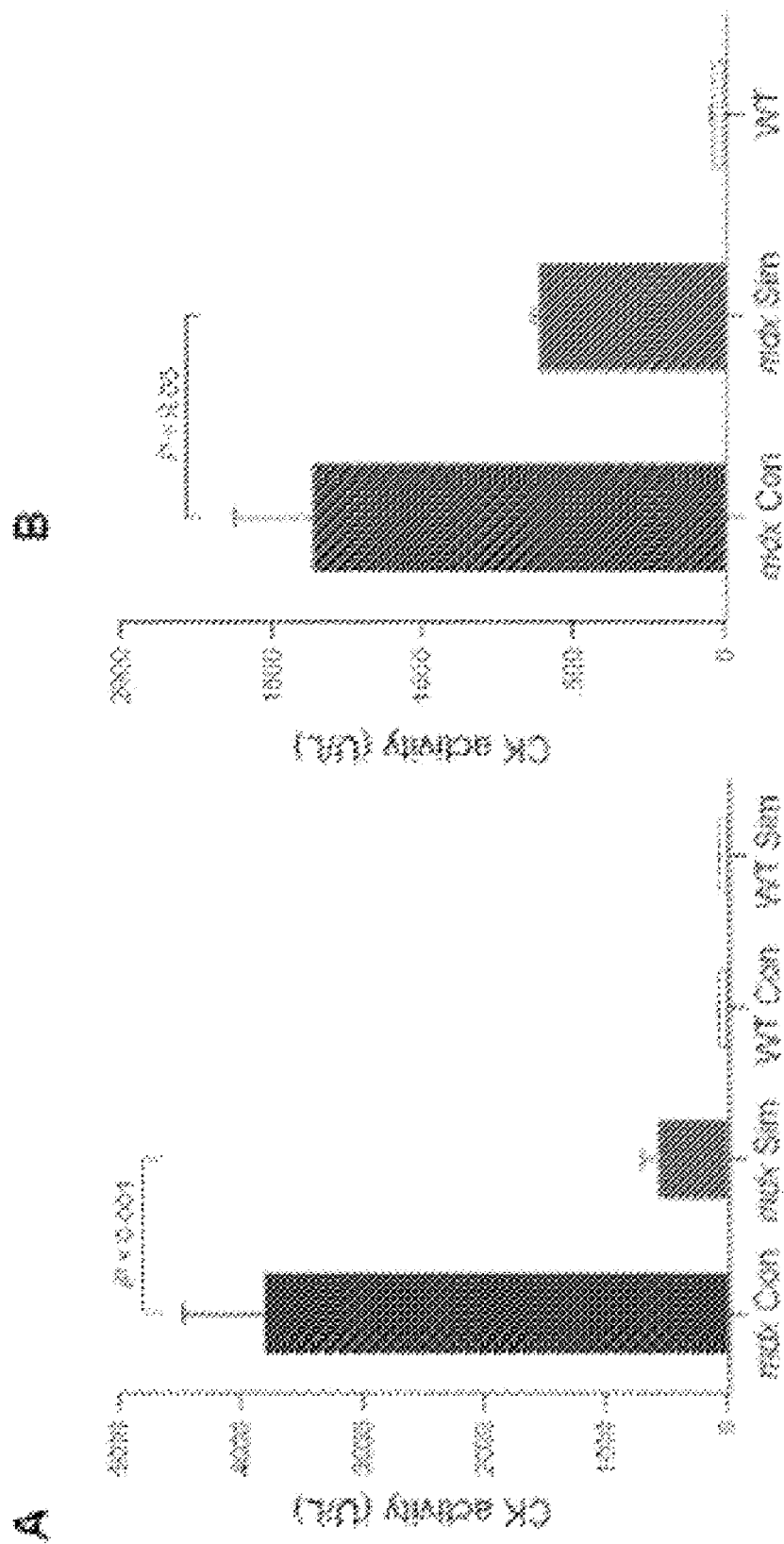
FIG. 7A shows plasma CK activity levels for WT and mdx mice with or without 8 months Simvastatin treatment.
FIG. 7B shows plasma CK activity levels for WT mice and mdx mice with or without 2 months Simvastatin treatment, starting at 12 months of age.

The activity levels of the mice were measured by voluntary running wheel activity over 2 days. On average, Simvastatin-treated mdx mice ran 20% more than control mdx mice, however this did not quite reach statistical significance (P=0.13). Therefore, since CK was measured after the running wheel activity, the dramatic reduction in CK levels in Simvastatin-treated mdx mice is not related to exercise levels. Also, WT mice treated with Simvastatin had similar activity levels as untreated WT mice, and there was no difference in CK levels between the two WT groups (FIG. 7A). Furthermore, regarding a time-dependent effect of Simvastatin on CK levels, we have recently found that in 12 month old mdx mice, 2 months of treatment significantly reduced CK levels compared to mdx Con mice (FIG. 7B). Therefore, statins cause a robust reduction in CK release from dystrophic muscle both in long-term treated mice starting from a young age (3 weeks to 8 months), and in old mice (12 months) over a 2 month period.

Example 2: Both Cardiac and Skeletal Muscle Benefit from Statin Treatment in the Mdx Model of DMD Duchenne muscular dystrophy (DMD) is a common, fatal, degenerative muscle disease that affects 1:3500 males worldwide. Currently there is no effective treatment for DMD. Skeletal and cardiac muscle degeneration in DMD is characterized by chronic inflammation, oxidative stress and fibrosis. Statins, the most widely used cholesterol lowering drugs, effectively inhibit these pathogenic processes in cardiovascular tissues, largely via cholesterol-independent, 'pleiotropic' mechanisms.

Statins have never been considered as a possible treatment for DMD or other muscular dystrophies principally because of the perceived risk of skeletal muscle damage, a known side effect of statins. Herein, we show unexpectedly that Simvastatin dramatically enhanced the physiological function of both skeletal and cardiac muscle of dystrophic mdx mice, an animal model of DMD. Long-term Simvastatin treatment vastly improved overall muscle health in mdx mice, reducing plasma CK activity, an established measure of whole-body muscle damage, to near-normal levels. This was accompanied by significantly less muscle inflammation and improved contractile force of the diaphragm muscle. Shorter-term treatment dramatically increased mdx hindlimb muscle force by 40%, provided resistance against muscle weakness from fatigue and reduced NADPH Oxidase 2 (NOX2) protein expression, a major source of oxidative stress and contractile dysfunction in mdx muscle. Finally, in older, more severely dystrophic mice, Simvastatin treatment decreased plasma CK activity, improved diaphragm force and halved pre-existing fibrosis. Moreover, Simvastatin reversed early-stage cardiac dysfunction, as evaluated by echocardiography. Improved cardiac function was associated with increased phosphorylation of phospholamban, a key regulatory protein of the Ca2+ pump (SERCA), a therapeutic target in DMD. Together, our findings demonstrate that statins, such as Simvastatin, provide considerable functional improvement to both skeletal and cardiac muscle of dystrophic mice and therefore can be used as a novel, affordable and readily available therapy for DMD and related neuromuscular diseases.

Duchenne muscular dystrophy (DMD) is a degenerative muscle disease caused by the absence of dystrophin, a large protein that links the cytoskeleton to the surface membrane in muscle cells. Loss of dystrophin causes widespread effects on muscle signaling and metabolic pathways, leading to cell death and progressive replacement of functional muscle fibers with fibrotic connective tissue. This results in profound muscle weakness, usually leaving DMD boys wheelchair-bound by their early teenage years and dead from the consequences of respiratory and/or cardiac muscle failure by age 20 to 30. Current treatments, such as corticosteroids, slow disease progression only marginally. Novel therapeutic approaches that target both skeletal and cardiac muscle are required to improve muscle health and longevity.

HMG CoA-reductase inhibitors (statins) are one of the most commonly prescribed classes of drugs for treating cardiovascular disease worldwide. While statins were originally designed to improve cardiovascular health by lowering circulating LDL cholesterol levels, more recent evidence indicates a wide range of additional benefits can be ascribed to the targeting of cholesterol-independent or 'pleiotropic' pathways, such as oxidative stress, inflammation and fibrosis. Interestingly, these deleterious pathways are known to be major contributors to the pathogenesis of DMD. To date, statins have not been tested in DMD or, indeed, any other neuromuscular disease. This is most likely due to the widely held view that statins are toxic to skeletal muscle and can cause varying myopathic symptoms. Nonetheless, we evaluated the effectiveness of Simvastatin, a commonly used statin, on skeletal and cardiac muscle function in the mdx mouse, the most widely studied animal model of DMD.

Simvastatin was orally administered for 8 months starting from 3 weeks of age. The dose was calculated to be between 5-10 mg/kg/day. This would equate to ~20-40 mg/day for a 10 year old DMD boy weighing 30 kg, based on mouse to human equivalence calculations, which is within the recommended dose range of statins for children. Whole-body muscle health was dramatically improved in Simvastatin-treated mdx mice (mdx Sim) compared to control mdx mice (mdx Con) as evidenced by an 85% reduction in plasma creatine kinase (CK) activity level, a commonly used marker of muscle damage. This measure of improved muscle health was confirmed by histological assessment of the tibialis anterior (TA) muscle, with mdx Sim muscles showing less evidence of muscle necrosis and inflammation. Of note, Simvastatin had no effect on CK levels or muscle histology of WT mice. We then quantified the amount of inflammation, a key feature of the dystrophic muscle pathology Immunofluorescence levels of CD68, an inflammatory cell marker, were considerably reduced in mdx Sim mice compared to mdx Con. We also assessed the physiological function of the diaphragm, the most severely affected muscle of mdx mice and a major cause of respiratory failure in DMD. Specific muscle force (force normalized to cross-sectional area) was significantly higher (20-25%) in mdx Sim compared to mdx Con mice, over the full range of stimulation frequencies, indicating a robust improvement in muscle strength.

We then evaluated the efficacy of Simvastatin on mdx hindlimb muscle function following Simvastatin treatment starting at 3 months of age and continuing for an additional 3 months. Hindlimb (TA) muscle physiology was measured in situ, which has the advantages of direct nerve stimulation and intact blood circulation. Specific muscle force increased significantly ($P<0.01$) by 40% for mdx Sim compared to mdx Con mice. Interestingly, this improvement in TA muscle strength is comparable to that provided by a current and effective dystrophin gene therapy approach. We also evaluated muscle fatigue resistance and recovery from fatigue, because this is a major cause of weakness in dystrophic muscle. TA muscle fatigue was assessed after 1 min and 2 min of repetitive tetanic contractions (2 sec apart). At 1 min, mdx Sim had significantly greater force than mdx Con mice (68% versus 53%, $P<0.05$, n=5). After 2 min, there was no difference between any groups, including WT mice. Recovery from muscle fatigue was measured every 2 min up to 10 min post fatigue. There was significantly greater force recovery at 10 min for mdx Sim compared to mdx Con mice ($P<0.05$, n=5). Also, values for mdx Sim mice were not statistically different from WT mice, demonstrating that Simvastatin normalized muscle fatigue and recovery to WT levels in dystrophic mice.

In contrast to humans, statins are usually ineffective at lowering circulating LDL cholesterol levels in mice, except when specific genetic and/or dietary changes are imposed. Nevertheless, in order to determine whether or not the beneficial effects of Simvastatin were related to circulating cholesterol levels, we measured the plasma LDL plus VLDL (LDL/VLDL) as well as HDL cholesterol concentrations. Interestingly, mdx Con mice had significantly higher LDL/VLDL levels than WT mice, consistent with elevated serum cholesterol levels in DMD individuals. However, Simvastatin did not lower LDL/VLDL in mdx or WT mice. HDL cholesterol was not significantly different among any groups. These data indicate that the improved muscle function in mdx Sim mice is not attributable to a plasma cholesterol-lowering effect of Simvastatin. Oxidative stress is a central mechanism underlying the pathophysiology of DMD. Recent evidence from us and others has identified NADPH oxidase 2 (NOX2) as the major source of increased reactive oxygen species (ROS) production in dystrophic skeletal muscle, which in turn triggers excessive Ca2+ entry into muscle fibres by activation of stretch-activated channels. NOX2 expression was significantly decreased ($P<0.01$, $n=7$) in TA muscles of mdx Sim versus mdx Con mice. NOX2 expression was also decreased in WT Sim mice, indicating a common inhibitory effect of Simvastatin on muscle NOX2 protein levels. Importantly, NOX2 expression negatively correlated with TA specific force production, including values for both mdx and WT groups ($R2=0.77$, $P<0.001$), consistent with a recent study showing improved force production by mdx muscle after genetic ablation of a NOX2 regulatory subunit.

In order to be a viable treatment approach for DMD, a drug must be efficacious at different stages of the disease and target both skeletal and cardiac muscle. Therefore, we tested Simvastatin in old mdx mice, starting at 12 months of age, at which time skeletal muscle degeneration is advanced and cardiac dysfunction is evident by echocardiography. First, to assess whole-body muscle damage we measured plasma CK activity after 2 months of Simvastatin treatment. As in younger mice, we found significantly reduced CK levels in mdx Sim mice compared to mdx Con, indicating that Simvastatin protected against muscle fibre degeneration. Diaphragm force production progressively declines with age in both mdx mice and DMD. In old mdx mice, Simvastatin treatment improved diaphragm force by 20-30% over a wide-range of stimulation frequencies compared with untreated mdx mice. The replacement of muscle fibers with fibrotic connective tissue is a major cause of impaired muscle force generation in DMD and therefore an important therapeutic target. Importantly, the enhanced diaphragm force with Simvastatin treatment was accompanied by a considerable reduction in fibrosis, as visualized with a collagen stain. Quantification of total collagen I levels by hydroxyproline assay indicated a 50% reduction in fibrosis for mdx Sim mice. The levels of fibronectin, another fibrotic marker 3, were also significantly reduced in mdx Sim diaphragm sections. Since diaphragm fibrosis is extensive in mdx mice at this age, our data indicate that Simvastatin actually reversed pre-existing fibrosis, consistent with findings in cardiac muscle.

Figure 9A:
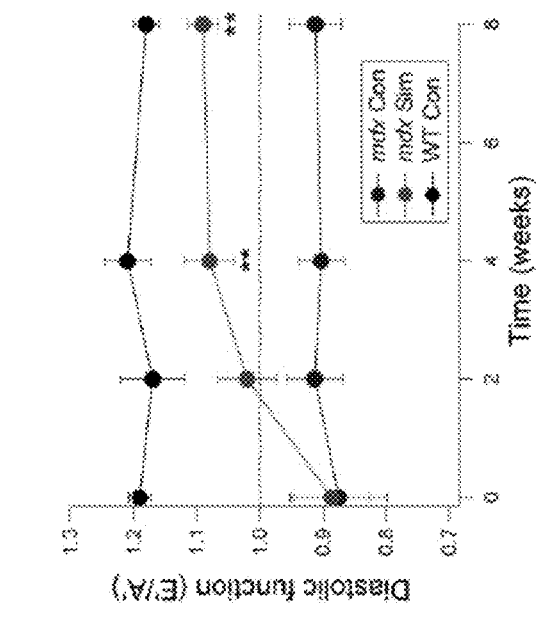
FIGS. 9A-9D show Simvastatin treatment of old mdx mice reverses cardiac muscle dysfunction and increases expression of PLB S-16, a key regulator of SERCA2A activity. In these experiments, mice were treated with Simvastatin starting at 12 months of age for a total of 2 months.
Figure 9B:
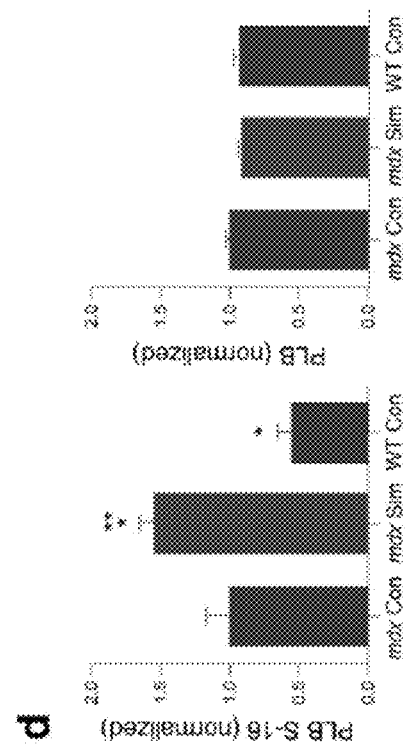

While respiratory muscle weakness remains a major cause of mortality in DMD, recent advancements in mechanical ventilation, and therefore greater life expectancy, has increased the prevalence of cardiac dysfunction in older DMD individuals. Cardiac disease in DMD is characterized by early diastolic dysfunction, which progresses to dilated cardiomyopathy. In DMD boys as young as 10, early signs of cardiac dysfunction can be detected by echocardiography, as evaluated by the myocardial performance index (MPI), a global measure of left ventricular systolic and diastolic function. Interestingly, in the same study, more commonly used parameters such as percent ejection fraction (EF %) and fractional shortening (FS %) were not different in DMD compared to control subjects. This demonstrates that MPI is a more sensitive measure of early cardiac dysfunction in DMD and is also an independent, predictive measure of mortality in children with idiopathic dilated cardiomyopathy. In mdx mice, MPI is significantly increased by 12 months of age compared to WT mice, indicating left ventricular dysfunction. Therefore, we investigated whether Simvastatin could reverse early cardiac dysfunction in mdx mice, using MPI as the main parameter. Remarkably, mdx Sim mice had a progressive decrease in MPI that approached WT levels after 2 months of treatment, while mdx Con mice remained unchanged over this period (FIG. 9A). We also measured diastolic function using tissue Doppler imaging to determine the ratio of the early diastolic velocity (E') to peak atrial velocity (A'). The E'/A' ratio was previously shown to be <1.0 in 12 month old mdx mice, indicating diastolic dysfunction. Here, the E'/A' ratio was <1.0 in mdx Con mice but this value significantly increased above 1.0 in mdx Sim mice (FIG. 9B). Interestingly, other commonly used parameters, FS % and EF % were not different between the groups, consistent with the findings in young DMD boys. Together, this data indicates that Simvastatin reversed early left ventricular dysfunction in mdx mice, largely by improving the abnormal diastolic function.

Figure 9C:
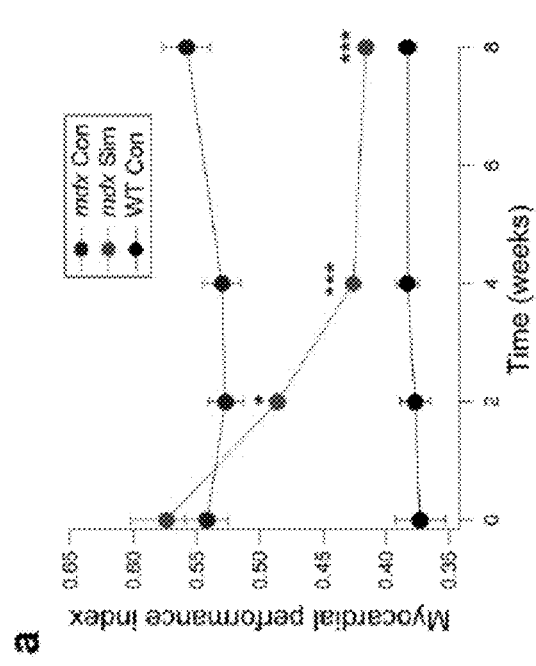
Figure 9D:
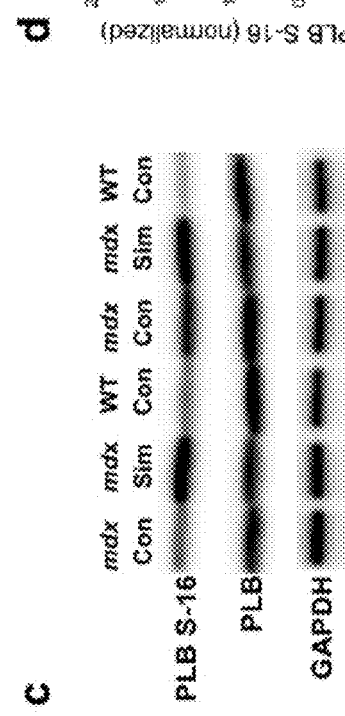

Aberrant Ca2+ handling in dystrophic cardiomyocytes leads to impaired relaxation, which is a major cause of diastolic dysfunction. Recently, transgenic expression of the sarcoplasmic/endoplasmic reticulum Ca2+ ATPase 2A (SERCA2a) was shown to improve cardiac function in old mdx mice. Therefore, we measured the expression level of SERCA2a in Simvastatin-treated and control mdx mice; however, there was no significant difference ($P=0.30$). Phospholamban (PLB) is a major inhibitor of SERCA activity and can therefore depress cardiac function. Unphosphorylated PLB binds SERCA and inhibits its activity, while phosphorylation at serine 16 (PLB S-16) relieves the inhibition of SERCA and enhances activity of the Ca2+ pump Immunoblotting demonstrated that PLB S-16 was significantly increased by 55% ($P<0.05$) following Simvastatin treatment compared to mdx Con, while total PLB (PLB) was not different between the groups (FIGS. 9C, 9D). PLB S-16 was also increased in mdx Con compared to WT, consistent with a recent finding in younger mdx mice. Thus, while the cellular mechanisms remain to be elucidated, it is plausible, without wishing to be bound or limited by theory, that greatly increased PLB S-16 levels in cardiac muscle of mdx Sim mice lead to enhanced SERCA2a activity, thereby providing a mechanism for the improved diastolic function. In support of this idea, it was shown that transgenic expression of a pseudophosphorylated form of PLB S-16 greatly enhanced cardiac function in a dystrophic hamster model with dilated cardiomyopathy.

In summary, the results described herein reveal that treatment of mdx mice with statins, such as Simvastatin, provides a dramatic reduction in the key pathogenic pathways, inflammation, oxidative stress and fibrosis, which lead to skeletal muscle degeneration and functional impairment in DMD. In addition, evidence is provided herein for a novel statin-induced therapeutic pathway in dystrophic cardiac muscle, the increased expression of PLB 5-16. Most importantly, these mechanistic effects translated into a remarkable improvement of both skeletal and cardiac muscle physiological function. Targeting both skeletal and cardiac muscle is a key requirement for the effective treatment of DMD. From a translational perspective, several statins, including Simvastatin, are FDA approved for the treatment of familial hypercholesterolemia in children as young as 10 years of age. Importantly, in clinical studies, statins were well tolerated by children with no significant side effects—including muscle complaints—compared to placebo controls. Thus, our findings indicate that statins can be used to provide a novel, safe, and readily available therapy for DMD and other related neuromuscular diseases.

Example 3

Duchenne muscular dystrophy (DMD) is a lethal, degenerative muscle disease with no effective treatment. DMD muscle pathogenesis is characterized by chronic inflammation, oxidative stress and fibrosis. Statins, cholesterol-lowering drugs, inhibit these deleterious processes in ischemic diseases affecting skeletal muscle, and therefore have potential to improve DMD. However, statins have not been considered for DMD, or other muscular dystrophies, principally because skeletal muscle-related symptoms are rare but widely publicized side effects of these drugs. Herein, we show positive effects of statins in dystrophic skeletal muscle. Simvastatin dramatically reduced damage and enhanced muscle function in dystrophic (mdx) mice. Long-term simvastatin treatment vastly improved overall muscle health in mdx mice, reducing plasma CK activity, an established measure of muscle damage, to near normal levels. This was accompanied by reduced inflammation, more oxidative muscle fibers, and improved strength of the weak diaphragm muscle. Shorter-term treatment protected against muscle fatigue and increased mdx hindlimb muscle force by 40%, a value comparable to current dystrophin gene-based therapies. Increased force correlated with reduced NADPH Oxidase 2 protein expression, the major source of oxidative stress in dystrophic muscle. Finally, in old mdx mice with severe muscle degeneration, simvastatin enhanced diaphragm force and halved fibrosis, a major cause of functional decline in DMD. These improvements were accompanied by autophagy activation, a recent therapeutic target for DMD, and less oxidative stress. Together, the findings described herein demonstrate that statins, such as simvastatin, substantially improve the overall health and function of dystrophic skeletal muscles and provide an unexpected, novel therapy for DMD and related neuromuscular diseases.

Duchenne muscular dystrophy (DMD) is a degenerative muscle disease caused by the absence of dystrophin, a large protein that links the cytoskeleton to the surface membrane in muscle cells. Loss of dystrophin causes widespread effects on muscle signaling and metabolic pathways, leading to cell death and progressive replacement of functional muscle fibers with fibrotic connective tissue. This results in profound muscle weakness, usually leaving DMD boys wheelchair-bound by their early teenage years and leading to death from the consequences of respiratory and/or cardiac muscle failure by age 20 to 30. Current treatments, such as corticosteroids, slow disease progression only marginally, while gene-based approaches, such as exon-skipping, although promising in pre-clinical studies, will need to overcome many technical and regulatory hurdles, as well becoming affordable, before they are a widely available therapy for DMD patients. Therefore, efficacious pharmaceutical agents that are cost effective and already approved for human use are particularly attractive candidates for the current treatment of DMD.

In DMD patients and dystrophin-deficient (mdx) mice, muscle degeneration has been attributed to a number of pathogenic processes, however chronic inflammation, oxidative stress and fibrosis certainly have major impacts on the disease progression and functional impairment. HMG CoA-reductase inhibitors (statins) are the most commonly prescribed drugs for treating high blood LDL cholesterol levels and associated cardiovascular diseases. A number of studies have shown that statins improve the cardiovascular system both by lowering circulating LDL cholesterol levels, as well as through cholesterol-independent or 'pleiotropic' mechanisms that lead to reduced oxidative stress, inflammation and fibrosis. Therefore, we reasoned that if statins inhibited these same pathogenic pathways in dystrophic muscle, these drugs would result in reduced muscle damage and improved physiological function.

Prior to the present study, statins had never been tested in DMD or any other neuromuscular disease. Indeed, statins are typically avoided in patients with muscle diseases because of the muscle-related side effects that occur with statin use in the general population. The causes of statin-induced myopathy are unclear, although several mechanisms have been postulated, including increased oxidative stress and activation of the atrogin-1 muscle atrophy pathway.

In the present study we treated DMD (mdx) mice with simvastatin, a lipophilic statin known to be effectively transported into skeletal muscle fibers. Using a simvastatin concentration that equates to a moderate daily dose in humans, we show that both long and short-term treatment in mdx mice provides robust improvement in muscle pathology and physiological function, which was accompanied by reduced inflammation, oxidative stress and fibrosis. We also provide evidence that statin treatment in dystrophic mice does not impede muscle regeneration or induce pathways thought to cause statin myopathy in humans. These results provide a paradigm shift by demonstrating for the first time that statins are beneficial in a degenerative skeletal muscle disease. These data indicate that statins have great potential to improve muscle health and function in DMD and related neuromuscular diseases.

Figures 10A, 10B, 10C, 10D, 10E:
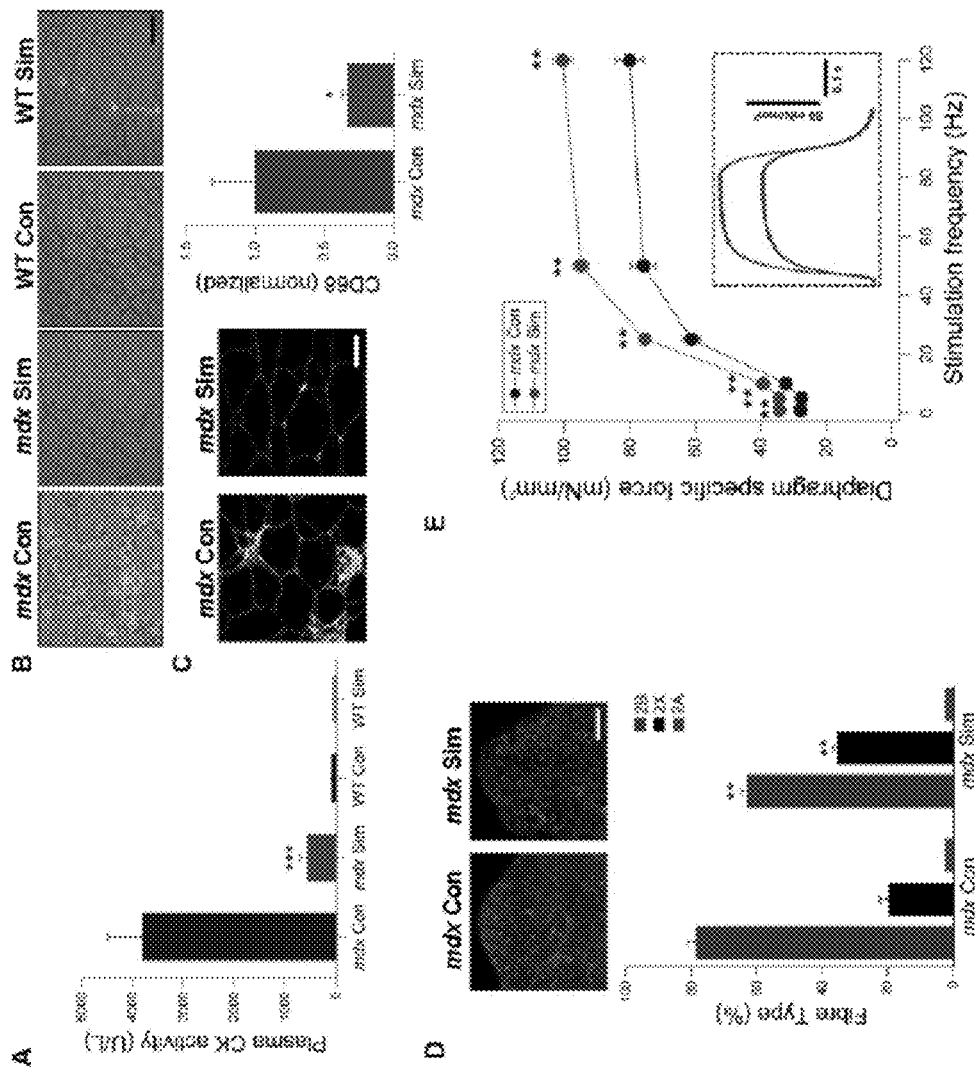
FIGS. 10A-10E show long-term Simvastatin treatment minimizes muscle damage and inflammation, shifts fiber type, and increases diaphragm muscle force in mdx mice. In these experiments, mice were treated with Simvastatin starting from weaning (3 weeks of age) for a total of 8 months.

Long-term simvastatin treatment protects dystrophic muscle from damage and inflammation while improving diaphragm function. DMD is a chronic, progressively degenerative disease and consequently potential treatments need to be effective over many years. Therefore, we first evaluated long-term simvastatin treatment in mdx mice, to determine both its effectiveness on the disease pathogenesis and also to assess any side-effects. Simvastatin was orally administered for 8 months starting from 3 weeks of age, which is just prior to the onset of muscle damage in mdx mice. The calculated dose given to the mice was between 5-10 mg/kg/day. This would equate to 20-40 mg/day for a 10 yea old DMD boy weighing 30 kg, based on mouse to human equivalence calculations, which is within the recommended dose range of statins for children. Whole-body muscle health was dramatically improved in simvastatin-treated mdx (mdx Sim) compared to control mdx mice (mdx Con) as evidenced by an 85% reduction in plasma creatine kinase (CK) activity level, a widely used clinical marker of muscle damage (FIG. 10A). This measure of improved muscle health was validated by histological assessment of the tibialis anterior (TA) muscle, which showed less muscle necrosis and inflammation in mdx Sim mice (FIG. 10B). Of note, simvastatin had no effect on CK levels or gross muscle histology of WT mice (see FIGS. 10A-10B), indicating there was no measureable muscle damage in normal mice at this moderate dose.

Next, we quantified the extent of inflammation, a key feature of the dystrophic muscle pathology, by immunofluorescence of TA muscle sections with CD68, a marker of macrophages and other inflammatory cells. Simvastatin substantially reduced inflammatory cell levels by close to 70% compared to mdx Con. These results are consistent with the known anti-inflammatory effects of statins in skeletal muscles of ischemic limbs.

The dystrophin homologue, utrophin, is upregulated and expressed along the sarcolemma in mdx muscles. Increase in utrophin can partially compensate for the loss of dystrophin and provide protection against muscle damage, making it a therapeutic target for DMD. Therefore, we sought to determine if the beneficial effects of simvastatin were related to enhanced expression of utrophin and/or other members of the dystrophin protein complex (DPC). However, western blotting results showed no additional increase in the expression levels of utrophin, other members of the dystrophin complex, or associated proteins such as nNOSµ and Caveolin-3. This indicates that the beneficial effects of simvastatin are not attributable to increased expression of utrophin or the dystrophin-associated protein complex.

Recent evidence has shown that metabolic changes can provide protection against damage in dystrophic muscle. In particular, shifting muscle fiber type from glycolytic type IIb fibers to more oxidative type IIa/x or very oxidative type I fibers by pharmacological or genetic approaches, reduces muscle damage and improves physiological function. Therefore, we measured the fiber type composition of TA muscle sections from mdx Con and mdx Sim mice. As shown in FIG. 10D, compared to mdx Con mice, TA muscles of mdx Sim mice displayed a significant fiber type shift of 15% from fast glycolytic IIb fibers to more oxidative, type IIX fibers. Interestingly, voluntary wheel running in mice also causes a fiber type shift from IIb to IIa/x, which is associated with improved endurance and enhanced oxidative metabolism.

In mdx mice, the diaphragm is the most severely affected skeletal muscle and diaphragm dysfunction is a major cause of respiratory failure in DMD. Therefore, we tested whether simvastatin improves diaphragm strength in mdx mice. Using isolated diaphragm muscle strips, specific muscle force (force normalized to muscle cross-sectional area) was significantly higher (20-25%) in mdx Sim mice compared to mdx Con, over the full range of stimulation frequencies (FIG. 10E), indicating a robust improvement in diaphragm physiological performance.

Simvastatin treatment enhances mdx hindlimb muscle force, which correlates with reduced NADPH oxidase 2 expression. Muscle degeneration and loss of function in DMD begins very early in the disease and progressively worsens over time. Consequently, useful therapeutic agents must be effective when administered at various stages of the disease. Therefore, we investigated whether simvastatin could improve muscle function, when given several months after the onset of muscle damage in mdx mice. Simvastatin treatment was started when mice were 3 months of age and measurements were performed 3 months later. Hindlimb (TA) muscle physiology was measured in situ. This method has the advantages of direct nerve stimulation and intact blood circulation, which provides an essentially in vivo approach for measuring muscle function. Remarkably, specific muscle force increased by 40% ($P<0.001$) for mdx Sim compared to mdx Con mice, a dramatic increase for a pharmacological agent. In fact, this 40% increase in specific force with simvastatin is comparable to that provided by the most effective gene-based therapeutic approaches, including a mini-dystrophin gene therapy construct containing the nNOS binding region, and antisense oligonucleotides (exon skipping), which led to homologous expression of a slightly truncated dystrophin protein throughout mdx TA muscle. Therefore, our data demonstrate that as a non-genetic approach, simvastatin provides a substantial improvement in contractile performance of dystrophic muscle. Interestingly, statin treatment also increases skeletal muscle specific force in an animal model of hindlimb ischemia, again emphasizing the point that statins augment muscle force production in specific disease conditions that are characterized by severe muscle damage and functional impairment.

Figures 11A, 11B, 11C, 11D:
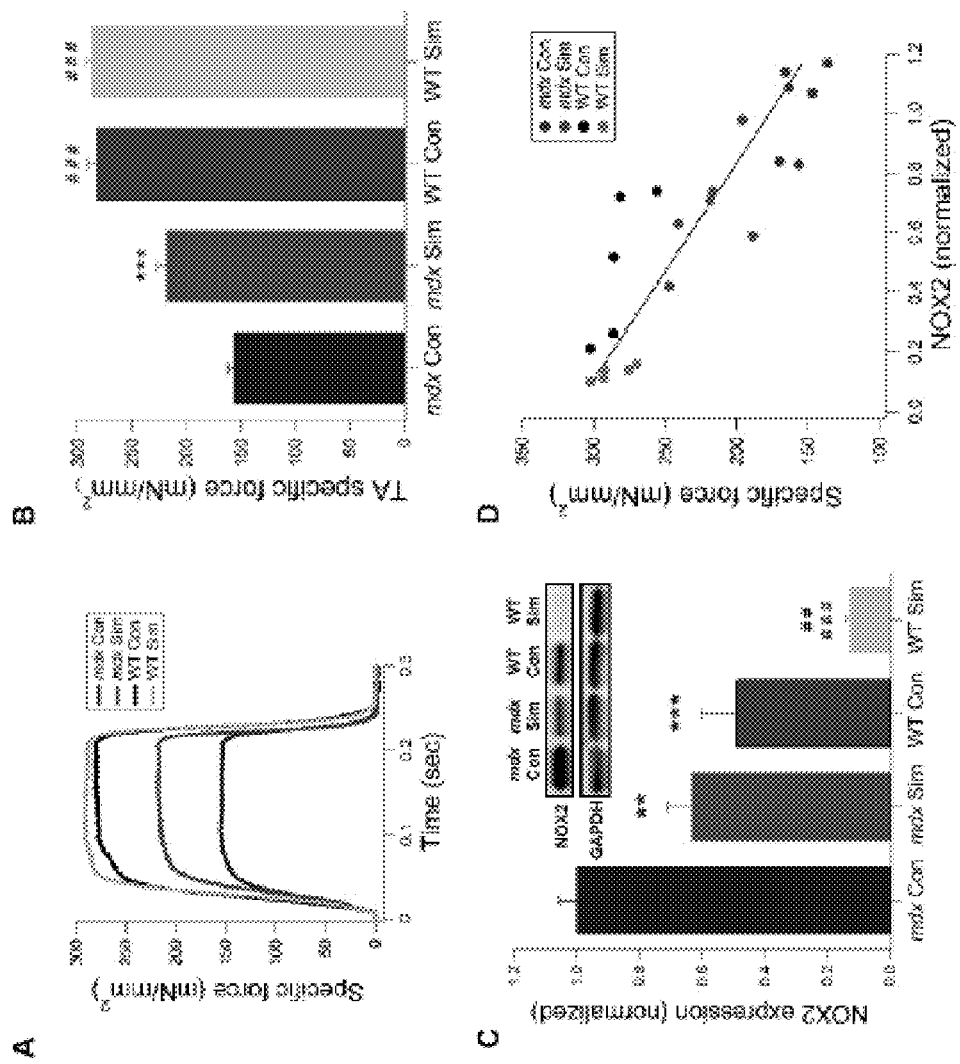
FIGS. 11A-11D show Simvastatin treatment enhances TA muscle force, normalizes muscle fatigue and reduces NOX2 expression in mdx mice. In these experiments, mice were treated with Simvastatin from 3 months up to 6 months of age.

Recent evidence by us and others has shown that oxidative stress due to increased reactive oxygen species (ROS) production by NADPH oxidase 2 (NOX2) is a major cause of muscle weakness in mdx mice. Since statins are known to inhibit NOX2-derived ROS in the cardiovascular system, we measured the NOX2 expression levels in TA muscles. Compared to mdx Con, mdx Sim mice had a significant reduction in NOX2 expression levels. NOX2 levels were also decreased in WT Sim mice, indicating a common inhibitory effect of simvastatin on skeletal muscle NOX2 protein levels. Importantly, there was a strong, negative correlation between NOX2 levels and TA specific force values ($R^2=0.76$; $P<0.001$, FIG. 11D). These data are consistent with a recent finding, showing improved force production by mdx muscle after genetic ablation of a NOX2 regulatory subunit.

Figures 12A, 12B, 12C:
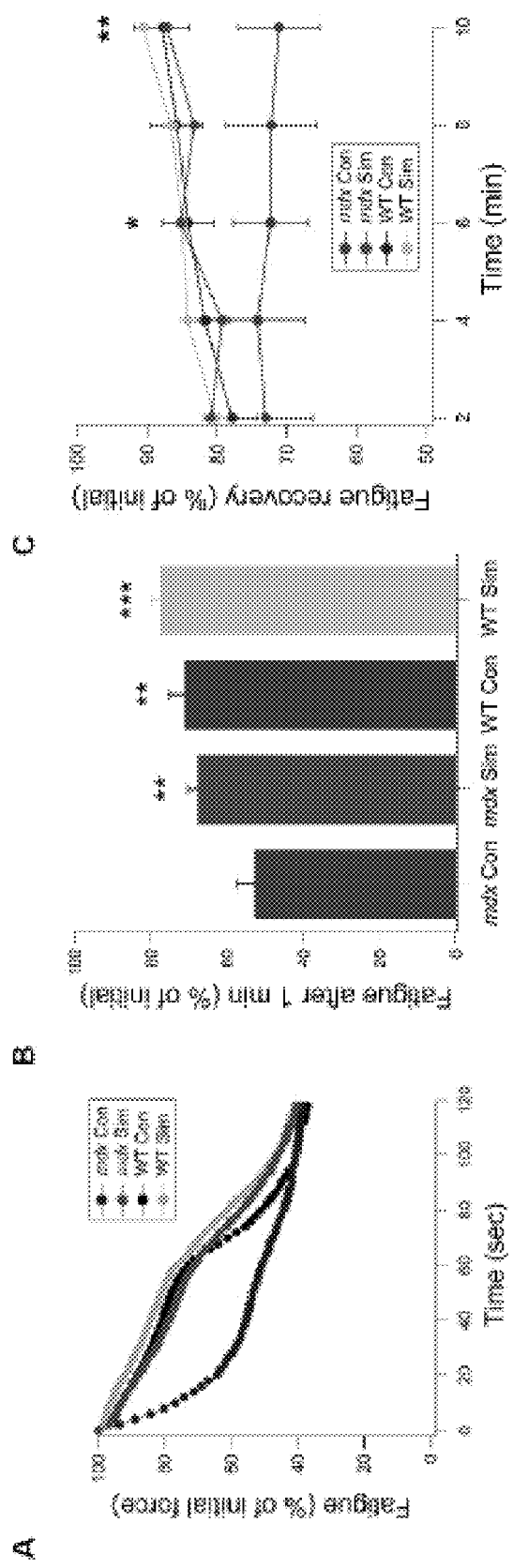
FIGS. 12A-12C show Simvastatin protects against muscle fatigue and improves force recovery in mdx mice. In these experiments, mice were treated with Simvastatin from 3 months up to 6 months of age.

Simvastatin improves resistance to muscle fatigue in mdx mice. In addition to the loss of specific force, increased muscle fatigue and slowed force recovery are also significant causes of muscle weakness in DMD. Muscle fatigue in TA was measured during repetitive tetanic contractions (every 2 seconds) for a total of 2 minutes. For mdx Con mice, force declined rapidly during the early part of the fatigue and then much less steeply for the remainder of the contractions (FIG. 12A). In contrast, the force decline for mdx Sim was very similar to the WT groups, with a slow force drop over the first minute and then a greater decline over the last minute (see FIG. 12B). After 1 minute of fatigue, mdx Sim had significantly greater force than mdx Con mice (68% versus 53% of initial force, $P<0.05$, FIG. 12B). After 2 minutes, there was no difference between any groups, including WT mice (see FIG. 12B). Recovery from fatigue was measured up to 10 min post fatigue (FIG. 12C). For mdx Con mice, the average recovery at 2 min was 3% of the initial, pre-fatigue force compared to 80.9% for mdx Sim mice. By 10 min, there was no further recovery for mdx Con but values for mdx Sim mice increased to 86.9% and were significantly different ($P<0.05$). Values for mdx Sim mice were not statistically different from both WT groups, indicating that simvastatin normalizes muscle fatigue and recovery to WT levels in dystrophic mice. The cellular mechanisms of muscle fatigue are complex, however ROS are known to be an important cause of force loss during muscle fatigue. As for specific force, we also found that NOX2 levels (see FIG. 11C), negatively correlated with muscle force after 1 minute of fatigue ($R^2$ adjusted=0.48, $P<0.001$). Therefore, it is likely that reduced ROS production from NOX2 contributes to the improved fatigue resistance in simvastatin treated mdx mice.

Plasma LDL cholesterol is higher in mdx mice but not reduced by simvastatin. In contrast to humans, statins are usually ineffective at reducing the naturally low, circulating LDL cholesterol levels in mice, except when specific genetic and/or dietary changes are made. Nevertheless, to determine if the beneficial effects of simvastatin on TA muscle function were associated with reduced circulating cholesterol levels, we measured the plasma LDL and VLDL (LDL/VLDL) as well as HDL cholesterol concentrations. Interestingly, mdx Con mice had significantly higher LDL/VLDL levels than WT mice, in accordance with elevated serum cholesterol levels in DMD individuals. However, simvastatin did not lower LDL/VLDL in mdx or WT mice. HDL cholesterol was not significantly different among any groups. These data indicate that the improved muscle function in mdx Sim mice is not attributable to a plasma cholesterol-lowering effect of simvastatin.

Figures 13A, 13B, 13C, 13D, 13E:
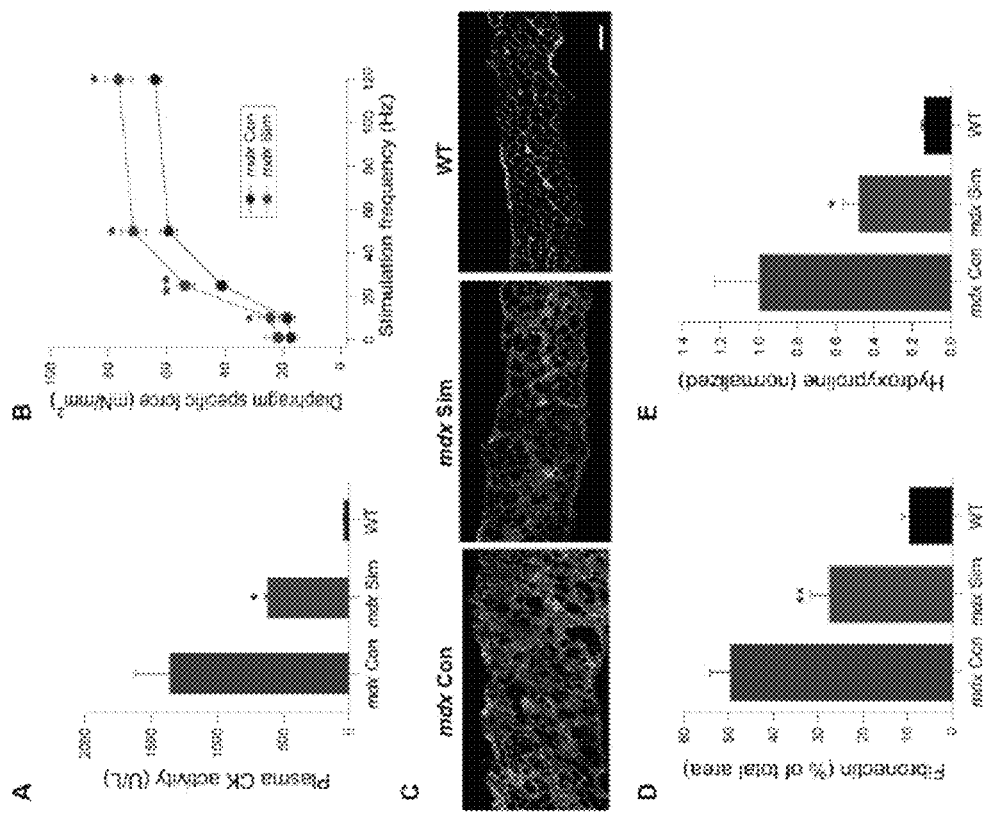
FIGS. 13A-13E show Simvastatin treatment in old mdx mice attenuates muscle damage, improves diaphragm force and reduces fibrosis. In these experiments, mice were treated with Simvastatin starting at 12 months of age for a total of 2 months.

Simvastatin improves diaphragm muscle function in old mdx mice and reverses fibrosis in mdx mice. The diaphragm most closely recapitulates the functional deficits and fibrotic deposition that occur in DMD. Therefore, we treated old mdx mice with simvastatin, to determine if it could improve diaphragm force and reduce or reverse pre-existing fibrosis. As with younger mice (see FIG. 10A), old mdx mice treated with simvastatin for 2 months had significantly lower plasma CK levels, indicating protection against ongoing muscle damage (FIG. 13A). Diaphragm specific force was also significantly improved by 20-30% over a wide-range of stimulation frequencies (10 to 120 Hz), compared with untreated mdx mice (FIG. 13B). The replacement of muscle fibers with fibrotic connective tissue is a major cause of impaired muscle force generation in DMD and therefore an important therapeutic target. First, we evaluated fibrosis by fibronectin immunofluorescence of diaphragm sections (FIG. 13D), which revealed a dramatic (50%) attenuation of fibrosis in mdx Sim mice compared to mdx Con (FIG. 13D). Quantification of total collagen I levels in diaphragm muscles by hydroxyproline assay also indicated a 50% reduction in fibrosis for mdx Sim mice (FIG. 13E). Since diaphragm connective tissue deposition is already extensive in mdx mice at this age, our data indicate that simvastatin likely reversed some of the preexisting fibrosis, consistent with findings of statin treatment in fibrotic cardiac muscle.

Physiological concentrations of simvastatin do not impair muscle regeneration or myogenesis in mdx muscle. It has been suggested that statins, including simvastatin, impair muscle regeneration by impeding myoblast differentiation. However, the statin concentrations required to induce these deleterious effects in vitro are typically 1 µM or greater. These concentrations are considerably (100-1000 times) higher than those found in vivo in mice and humans. In the present study, we measured the plasma levels of simvastatin in treated mdx mice, which were, on average 403±108 nM (n=7). In treated rats, the simvastatin concentration in skeletal muscle relative to plasma is 30%. Therefore, we would expect the muscle levels of simvastatin in our mice to be 120 nM. At this concentration, we found that muscle regeneration in vivo was unaffected in mdx Sim mice, as they had a comparable number of centrally nucleated (regenerated) muscle fibers as mdx Con mice after long-term (8 months) treatment. We then carried out an in vitro experiment using an immortalized mdx myoblast cell line. At the start of differentiation, we treated the cells with a range of simvastatin concentrations for 3 days, and found that muscle differentiation, in terms of myotube formation, appeared similar to untreated cells at concentrations ranging from 50 to 500 nM. In accord with previous studies, at doses of 1 µM or higher, simvastatin became more toxic and the number of viable cells progressively decreased over 3 days of treatment. Again, this highlights the point that simvastatin concentrations within the normal, in vivo physiological range do not impair myogenesis in dystrophic muscle cells and deleterious effects only occur with exposure to much higher doses.

Figures 14A, 14B, 14C:
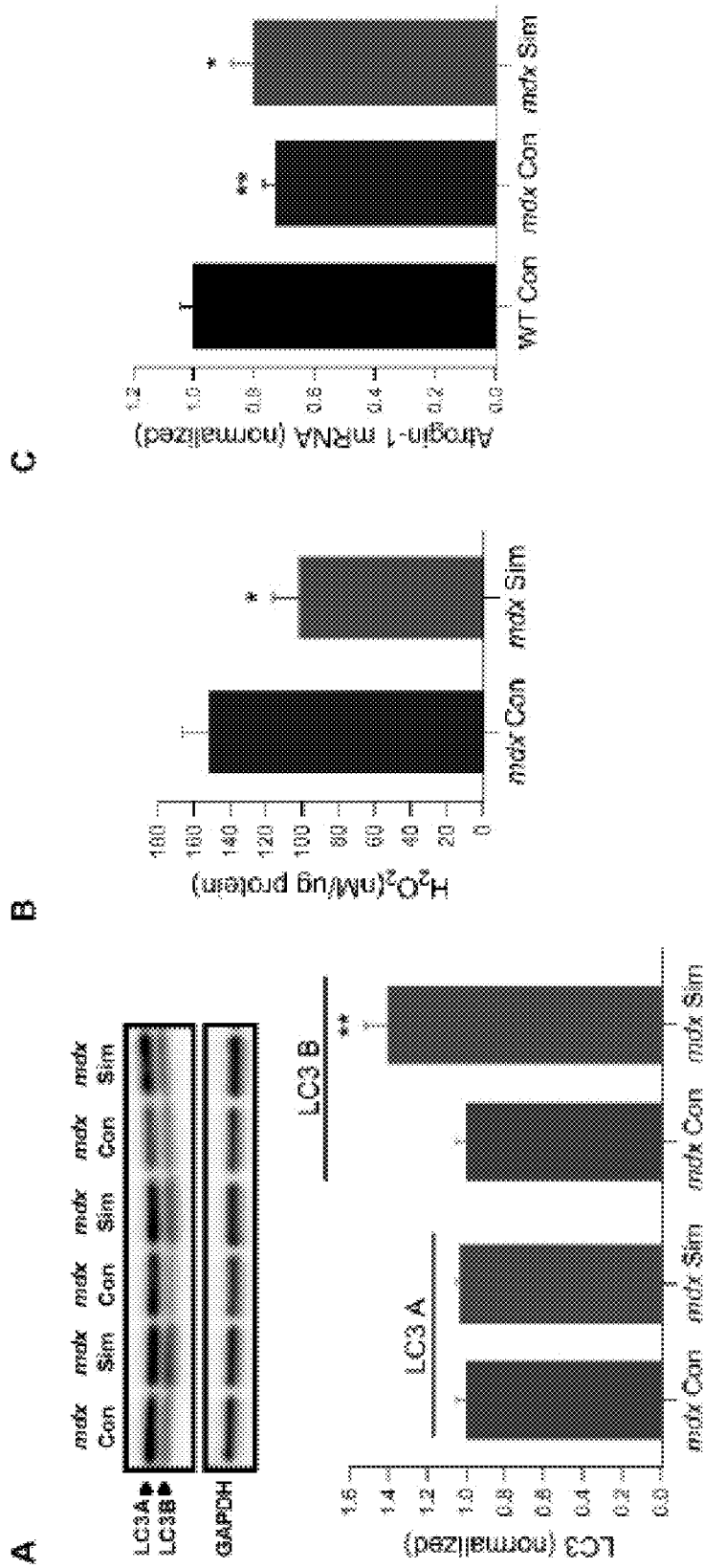
FIGS. 14A-14C show Simvastatin treatment in old mdx mice enhances autophagy, attenuates ROS levels and does not induce atrogin-1. In these experiments, mice were treated with Simvastatin starting at 12 months of age for a total of 2 months.

Simvastatin enhances autophagy and reduces oxidative stress but does not simulate atrogin-1 in mdx muscle. Autophagy is an important cellular pathway for degrading damaged proteins, organelles and protein aggregates, which are then recycled by the cell for energy use. Impaired autophagy can trigger cell death and in skeletal muscle, proper regulation of autophagy is essential for normal cellular and physiological function. Both mdx and DMD muscles show evidence of reduced autophagy and treatment of mdx mice with a low protein diet triggered autophagy, which reduced inflammation and fibrosis and enhanced muscle function. Simvastatin was recently shown to enhance autophagy in arterial myocytes (43) and therefore, we postulated that increased autophagy might contribute to the improved muscle health in mdx mice. A key protein marker of autophagic flux is the microtubule-associated protein 1A/1B light chain 3, which has a cytosolic form (LC3A) and a lapidated form (LC3B). An increased level of LC3B relative to LC3A is indicative of enhanced autophagic flux. We measured LC3A and LC3B expression in the diaphragm of simvastatin treated and untreated mdx mice, using an antibody that detects both protein isoforms. As shown in FIG. 14A, the levels of LC3A were not different between the groups, however LC3B was significantly increased by 40% in mdx Sim mice (P<0.01), signifying enhanced autophagy. This result is consistent with the increased levels of LC3B by simvastatin in arterial myocytes.

Interestingly, recent evidence revealed that NOX2-derived ROS plays a key role in reducing autophagy in mdx muscle. Therefore, our data showing reduced NOX2 expression by simvastatin is consistent with its autophagy enhancement of dystrophic muscle. To further explore this idea, we also measured the levels of the ROS (H2O2) in diaphragm muscle homogenates. We found that mdx Sim muscles had 30% less H2O2 compared to mdx Con (FIG. 14B), indicative of reduced oxidative stress. This highlights important differences between dystrophic muscle, where statins reduce oxidative stress derived from NOX2, and normal muscle susceptible to statin myopathy, where mitochondrial ROS increases oxidative stress.

Another pathway that has been implicated in statin myopathy is muscle atrophy mediated by atrogin-1, a ubiquitin-protein ligase that stimulates protein breakdown. Atrogin-1 is induced by statin treatment in animal models and humans with statininduced myopathy. However, in DMD, atrogin-1 levels are consistently lower than in normal muscle and are not increased at any stage of the disease. We quantified mRNA levels of atrogin-1 by qPCR in quadriceps muscles of old mice and also found that levels in mdx Con were significantly lower than for WT (FIG. 14C). Interestingly, values for mdx Sim mice were also lower than WT and not significantly different from mdx Con (see FIG. 14C). These data indicate that atrogin-1 is not induced in dystrophic muscle by simvastatin. Again, this emphasizes the opposite effect of simvastatin on a pathogenic pathway in dystrophic skeletal muscle compared to normal muscle.

In summary, the results described herein reveal for the first time that treatment of dystrophic mdx mice with simvastatin provides a dramatic reduction in inflammation, oxidative stress and fibrosis, key pathogenic pathways that mediate skeletal muscle damage and functional impairment in DMD. Most importantly, these mechanistic effects translated into a substantial improvement in skeletal muscle physiological function, both in terms of specific force production and protection from muscle fatigue. The data described herein is unexpected but consistent with the idea that statins are highly beneficial to skeletal muscles afflicted with an underlying disease that involves ischemia, oxidative stress and inflammation.

From a clinical perspective, several statins, including simvastatin, are already FDA approved for the treatment of familial hypercholesterolemia in children as young as 10 years of age. Thus, the novel findings described herein indicate that simvastatin and other statins provide a readily available therapy for DMD and related neuromuscular disease.

Methods

Male dystrophin-deficient (mdx) and wild type (WT) mice on the C57BL/10ScSn background were used for all experiments, which were approved by the Institutional Animal Care and Use Committee (IACUC) at the University of Washington.

Simvastatin powder (TCI America) was formulated as a treatment in two ways; in the drinking water and in the food. The inactive form of simvastatin contains a lactone group and is relatively insoluble in water. Therefore, for the drinking water experiments, simvastatin (50 mg) was initially dissolved in 1 ml of ethanol and then mixed for several minutes into 1 L of alkaline water (pH 10), which hydrolyzes the lactone group, enabling the active (hydroxy acid) form of simvastatin to be solubilized in water. Hydrochloric acid was then added to lower the pH to 2.5-3.0, which was the pH of the drinking water given to the control (untreated) mice. For formulation into the food, simvastatin (lactone form) was mixed into a standard rodent diet (D12450B) at a concentration of 80 mg/kg (Research Diets Inc., New Jersey).

Diaphragm function, ex vivo, was measured as described previously. Briefly, diaphragm strips (2-3 mm wide) were perfused with a physiological solution bubbled with 95% $O_2$-5% $CO_2$. Stimulation was provided by two platinum electrodes, attached along the sides of the chamber. A lengthforce curve, established using 120 Hz isometric contractions (300 ms duration spaced 1 min apart, established the optimum length (length producing maximum tetanic force), which was later used to calculate the specific force (force divided by cross-sectional area).

Tibialis anterior (TA) muscle function was measured in situ. Mice were anaesthetized with an intraperitoneal injection of Avertin (625 mg/kg) and placed on a heated metal platform (37° C.). The distal TA tendon was dissected free and sutured to the lever arm of the force and length control system (305C-LR, Aurora Scientific). Muscle contraction was provided by stimulation of the Sciatic nerve using bipolar electrodes, which was kept moist during the experiment with PBS. The knee bone was firmly anchored to the platform via a steel pin. A length-force curve was generated by stimulating the muscle at 120 Hz (200 ms duration), every 90 sec, from short to long muscle lengths. After establishing the optimum length, the muscle then underwent a fatigue protocol, in which it was stimulated at 120 Hz (200 ms duration) every 2 sec for a total of 2 min. Fatigue recovery was measured every 2 min up to 10 min post-fatigue. Western blotting was performed as described previously. Briefly muscles were homogenized in a PBS buffer containing EDTA (5 mM) and protease (Thermo Scientific) and phosphatase (Rhoche) inhibitor cocktail and 1% Triton X-100. Samples were loaded onto 4-15% gradient gels (Biorad) and transferred on PVDF membranes (Millipore). Membranes were blocked for 1 to 2 hrs with 5% skim milk in PBST or 2.5% BSA in PBST for phosphorylated proteins, and then incubated with primary antibodies in blocking buffer for 1 hr at room temperature or overnight at 4° C. Primary antibodies used were; NOX2, α-dystrobrevin 1 and 2, and caveolin 3 (BD Biosciences), LC3A/B (Biorad), utrophin and α-syntrophin (44), nNOS (Invitrogen), β-dystroglycan (Novocastra) and GAPDH (Santa Cruz Biotechnology). HRP labeled secondary antibodies were then incubated for 1 hr at room temperature. Membranes were incubated with enhanced chemiluminescence (ECL) reagent (Amersham) and bands were detected by the FluorChem M, imaging system (Protein Simple).

Muscles were imbedded in O.C.T compound and frozen in isopentane cooled in liquid nitrogen. Cryosections (10 μm thick) were placed on a glass side. Sections were fixed with either ice-cold methanol or 2% paraformaldehyde for 5 to 10 min. Some sections were stained with Haemotoxylin and Eosin (H & E) using standard procedures. For immunofluorescence, sections were incubated in blocking buffer (0.8% BSA and 1% fish gelatin in PBS) for 45 min. Primary antibodies; Fibronectin (Sigma), CD68 (Abcam), Caveolin3 (BD Biosciences), and Myosin Heavy Chain 1, 2A and 2B (Developmental Studies Hybridoma Bank) were added for 1 hr 30 min at room temperature. AlexaFluor conjugated secondary antibodies (Life Technologies) were then added for 1 hr 30 min. In some experiments, DAPI was also added to detect nuclei. Sections were mounted with anti-fade Gold reagent (Life Technologies) cover slipped and imaged with a Zeiss LSM510 confocal microscope (W.M. Keck Center, University of Washington) or a Zeiss Axioscop 2 fluorescent microscope. For fluorescence quantification (CD68, fibronectin and myosin heavy chains), images were converted to grayscale in Image J and a threshold applied to calculate the area of fluorescence as a percent of the total area of the section. Fibers with central nuclei were expressed as a percent of total fibers with detectable nuclei (ie. both central and peripheral).

To quantify muscle fibrosis, Collagen I content was measured using the hydroxyproline assay. Muscles were homogenized in the same PBS-Triton X100 buffer used for Western blotting. Samples were centrifuged at 9,500×g for 10 min. The pellet was used for hydroxyproline measurement. The supernatant was used to measure the total protein concentration (BCA assay) for later normalizing hydroxyproline values. The insoluble pellets, containing Collagen I, were placed into glass tubes with 200 μl of 6N HCl. Samples were boiled for 24 hours at 120° C. in a heat block. After vortexing and centrifuging at 10,000 rpm for 3 min, the supernatants were used for the hydroxyproline assay, using a commercial kit (Chondrex). Hydroxyproline values (μg/μl) were normalized to the total protein content of the muscle.

Plasma CK was evaluated as a measure of whole body muscle damage. Blood was drawn via submandibular puncture, collected into EDTA coated tubes (BD Microtainer) and centrifuged at 2,400×g for 12 min at 4° C. Plasma was then used to measure CK activity with a standard assay kit, according to the manufacturer's instructions (StanBio).

Immortomouse mdx myoblasts were grown on gelatin coated plates and until 70% confluence in DMEM supplemented with 10% HS, 20% FBS, 0.5% chicken embryo extract and 20 units/ml of γ-interferon. To induce differentiation into myotubes, cells were incubated with DMEM containing 5% HS, with or without different concentrations of simvastatin for three days. Myotubes were washed in PBS, fixed in ice-cold methanol for 10 min, and H&E stained. Images of myotubes were taken with a Nikon inverted microscope (W.M. Keck Center, University of Washington).

Total RNA was isolated from quadriceps of WT, mdx, and simvastatintreated mdx mice using Trizol (Life Technologies) and further purified using an RNAeasy Kit (Qiagen). Real-time quantitative RT-PCR (qPCR) was performed using TaqMan chemistry and the ABI 7000 sequence detection system with 50 ng of RNA, ABI Fast Virus 1-Step Master Mix reagents, and primer sets specific for atrogin-1 and HPRT (Applied Biosystems). Data were obtained from 5 mice in each treatment group and normalized to the internal HPRT control.

Using a commercial assay kit (Abcam), LDL/VLDL and HDL fractions were separated from plasma and mixed with an enzyme reaction solution containing a fluorescent probe, to quantify the amount of cholesterol in the sample. Fluorescence levels were measured with a spectrophotometer in a 96 well plate. Cholesterol values for each sample were determined from a cholesterol standard curve.

Simvastatin concentrations in the plasma of mdx mice treated from 3 to 6 months of age, were measured and analyzed. Simvastatin was extracted from plasma samples with methanol and cyheptamide. Briefly, 20 μl of plasma was mixed with 50 μl of methanol and 5 μl of cyheptamide (250 μg/ml in Methanol) was added. Samples were vortexed for 2 min, followed by centrifuging for 10 min at 14000 rpm. The supernatant was collected and used for analysis by HPLC/UV. The separation was performed on a Zorbax XDB-C8 column (50×2.1 mm, particle size 5 μm) (Agilent). The mobile phase consisted of A: H2O, B: MeOH. The flow rate was set to 0.6 ml/min and simvastatin was detected at UV wavelength 238 nm. Plasma samples from untreated mice were used as a negative control and for setting up the standard curve.

All data are presented as the mean±S.E.M. The significance level for all experiments was set at $P<0.05$. Unpaired student's t-test was used to compare values between two groups. One-way ANOVA with LSD post-hoc test was used for analysis of more than two groups. For analysis of CD68 immunostaining, the non-parametric Mann-Whitney U test was applied. For some variables, a linear regression analysis was performed. The statistical program used was Data Desk (Ithaca, N.Y., USA).

The particulars shown herein are by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice.

The following definitions and explanations are meant and intended to be controlling in any future construction unless clearly and unambiguously modified in the following examples or when application of the meaning renders any construction meaningless or essentially meaningless. In cases where the construction of the term would render it meaningless or essentially meaningless, the definition should be taken from Webster's Dictionary, 3$^{rd}$ Edition or a dictionary known to those of skill in the art, such as the Oxford Dictionary of Biochemistry and Molecular Biology (Ed. Anthony Smith, Oxford University Press, Oxford, 2004).

As used herein and unless otherwise indicated, the terms "a" and "an" are taken to mean "one", "at least one" or "one or more". Unless otherwise required by context, singular terms used herein shall include pluralities and plural terms shall include the singular.

Unless the context clearly requires otherwise, throughout the description and the claims, the words 'comprise', 'comprising', and the like are to be construed in an inclusive sense as opposed to an exclusive or exhaustive sense; that is to say, in the sense of "including, but not limited to". Words using the singular or plural number also include the plural and singular number, respectively. Additionally, the words "herein," "above," and "below" and words of similar import, when used in this application, shall refer to this application as a whole and not to any particular portions of the application.

The description of embodiments of the disclosure is not intended to be exhaustive or to limit the disclosure to the precise form disclosed. While the specific embodiments of, and examples for, the disclosure are described herein for illustrative purposes, various equivalent modifications are possible within the scope of the disclosure, as those skilled in the relevant art will recognize.

All of the references cited herein are incorporated by reference. Aspects of the disclosure can be modified, if necessary, to employ the systems, functions, and concepts of the above references and application to provide yet further embodiments of the disclosure. These and other changes can be made to the disclosure in light of the detailed description.

Specific elements of any foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

What is claimed:

1. A method of treating a neuromuscular disease comprising administering to a subject having or at risk for a neuromuscular disease selected from Duchenne muscular dystrophy or Becker muscular dystrophy, a therapeutically effective amount of a statin drug, wherein statin administration for treatment of neuromuscular disease is commenced before the subject is 10 years of age.

2. The method of claim 1, wherein the statin drug is a lipophilic statin drug.

3. The method of claim 2, wherein the lipophilic statin drug is selected from simvastatin, atorvastatin, cerivastatin, fluvastatin, lovastatin, and pitavastatin.

4. The method of claim 2, wherein the lipophilic statin drug is simvastatin.

5. The method of claim 1, wherein the statin drug is administered at a dose of 0.1 mg to 100 mg.

6. The method of claim 1 wherein the statin drug is administered in a lactone pro-drug form.

7. The method of claim 1, wherein the subject having or at risk for a neuromuscular disease has not been previously diagnosed with high cholesterol levels or has not been previously diagnosed with a cardiovascular disease.

8. The method of claim 1, wherein the subject having or at risk for a neuromuscular disease has not been previously diagnosed with familial hypercholesterolaemia.

9. A method of treating a neuromuscular disease comprising administering to a subject having or at risk for a neuromuscular disease selected from Limb-girdle muscular dystrophies, Ullrich congenital muscular dystrophy, inflammatory myositis, muscle atrophy, and Amyotrophic lateral sclerosis, a therapeutically effective amount of a statin drug, wherein statin administration for treatment of neuromuscular disease is commenced before the subject is 10 years of age.

10. The method of claim 9, wherein the statin drug is a lipophilic statin drug.

11. The method of claim 10, wherein the lipophilic statin drug is selected from simvastatin, atorvastatin, cerivastatin, fluvastatin, lovastatin, and pitavastatin.

12. The method of claim 10, wherein the lipophilic statin drug is simvastatin.

13. The method of claim 9, wherein the statin drug is administered at a dose of 0.1 mg to 100 mg.

14. The method of claim 9, wherein the statin drug is administered in a lactone pro-drug form.

15. The method of claim 9, wherein the subject having or at risk for a neuromuscular disease has not been previously diagnosed with high cholesterol levels or has not been previously diagnosed with a cardiovascular disease.

16. The method of claim 9, wherein the subject having or at risk for a neuromuscular disease has not been previously diagnosed with familial hypercholesterolaemia.

* * * * *